US007485458B2

(12) United States Patent
Colosi

(10) Patent No.: US 7,485,458 B2
(45) Date of Patent: *Feb. 3, 2009

(54) ACCESSORY FUNCTIONS FOR USE IN RECOMBINANT AAV VIRION PRODUCTION

(75) Inventor: Peter C. Colosi, Alameda, CA (US)

(73) Assignee: Genzyme Corporation, Framingham, MA (US)

( * ) Notice: Subject to any disclaimer, the term of this patent is extended or adjusted under 35 U.S.C. 154(b) by 220 days.

This patent is subject to a terminal disclaimer.

(21) Appl. No.: 11/043,312

(22) Filed: Jan. 26, 2005

(65) Prior Publication Data

US 2005/0164392 A1 Jul. 28, 2005

Related U.S. Application Data

(60) Continuation of application No. 10/177,871, filed on Jun. 19, 2002, now Pat. No. 6,897,063, which is a division of application No. 09/406,363, filed on Sep. 28, 1999, now Pat. No. 6,482,633, which is a continuation of application No. 08/745,957, filed on Nov. 7, 1996, now Pat. No. 6,004,797.

(60) Provisional application No. 60/006,402, filed on Nov. 9, 1995.

(51) Int. Cl.
*C12N 15/00* (2006.01)
(52) U.S. Cl. .................. 435/325; 435/320.1; 435/235.1; 435/363; 435/366; 435/367
(58) Field of Classification Search ........................ None
See application file for complete search history.

(56) References Cited

U.S. PATENT DOCUMENTS

| 5,173,414 | A | 12/1992 | Lebkowski et al. |
| 5,436,146 | A | 7/1995 | Shenk et al. |
| 5,753,500 | A | 5/1998 | Shenk et al. |
| 5,872,005 | A | 2/1999 | Wang et al. |
| 5,945,335 | A | 8/1999 | Colosi |
| 6,004,797 | A | 12/1999 | Colosi |
| 6,268,213 | B1 | 7/2001 | Samulski et al. |

FOREIGN PATENT DOCUMENTS

| FR | 2 707 664 A1 | 1/1995 |
| WO | WO 96/22378 A1 | 7/1996 |
| WO | WO 96/40240 | 12/1996 |

OTHER PUBLICATIONS

Colosi, Peter, et al., "AAV Vectors can be Efficiently Produced Without Helper Virus," Blood, vol. 86, No. 10, Suppl. 01, XP000614696, Nov. 15, 1995, p. 627A.
Carter, "Adeno-Associated Virus Helper Functions," Handbook of Paroviruses 1(13):255-282 (1990).
Carter, et al., "Properties of an Adenovirus Type 2 Mutant, Ad2dl807, Having a Deletion Near the Right-Hand Genome Terminus: Failure to Help AAV Replication," Virology 126:505-516 (1983).

Georg-Fries, et al., "Analysis of Proteins, Helper Dependence, and Seroepidemiology of a New Human Parovirus," Virology 134:64-71 (1984).
Handa, "Complementation of Adeno-Associated Virus Growth with Temperature-Sensitive Mutants of Human Adenovirus Typed 12 and 5," J. Gen. Virol. 29:239-242 (1975).
Hermonat, et al., "Use of Adeno-Associated Virus as a Mammalian DNA Cloning Vector: Transduction of Neomycin Resistance into Mammalian Tissue Culture Cells," PNAS 81:6466-6470 (1984).
Ishibashi, "The Potentiation of Type A Adeno-Associated Virus by Temperature-Sensitive Conditional-Lethal Mutants of CELO Virus at the Restrictive Temperature," Virology 45:317-320 (1971).
Ito, "Adeno-Associated Satellite Virus Growth Supported by a Temperature-Sensitive Mutant of Human Adenovirus," J. Gen. Virol. 9:243-245 (1970).
Janik, et al., "Locations of Adenovirus Genes Required for the Replication of Adenovirus-Associated Virus," Proc. Natl. Acad. Sci. USA 78(3):1925-1929 (1981).
Jay, et al., "Eukaryotic Translational Control: Adeno-Associated Virus Protein Synthesis is Affected by a Mutation in the Adenovirus DNA-Binding Protein," Proc. Natl. Acad. Sci. USA 78(5):2927-2931 (1981).
Javier, "Adenovirus Type 9 E4 Open Reading Frame 1 Encodes a Transforming Protein Requires for the Production of Mammary Tumors in Rats," Journal of Virology 68(6):3917 (1994).
Klessig, et al., "Introduction, Stable Integration, and Controlled Expression of a Chimeric Adenovirus Gene Whose Product is Toxic to the Recipient Human Cell," Molecular and Cellular Biology 4(7):1354 (1984).
Laughlin, et al., "Effect of Deletions in Adenovirus Early Region 1 Genes Upon Replication of Adeno-Associated Virus," J. Virol. 41(3):868-876 (1982).
McPherson, et al., "Human Cytomegalovirus Completely Helps Adeno-Associated Virus Replication," Virology 147:217-222 (1985).
Mishra, et al., "Adeno-Associated Virus DNA Replication is Induced by Genes that are Essential for HSV-1 DNA Synthesis," Virology 179:632-639 (1990).
Myers, et al., "Adenovirus Helper Function for Growth of Adeno-Associated Virus: Effect of Temperature-Sensitive Mutations in Adenovirus Early Gene Region 2," J. Virol. 35(1):65-75 (1980).
Myers, et al., "Adeno-Associated Virus Replication," J. Biol. Chem. 256(2):567-570 (1981).
Moore, et al., "Oncogenic Potential of the Adenovirus E4orf6 Protein," Proc. Natl. Acad. Sci. USA 93:11295-11301 (1996).
Ostrove, et al., "Adenovirus Early Region 1b Gene Function Required for Rescue of Latent Adeno-Associated Virus," Virology 104:502-505 (1980).

(Continued)

*Primary Examiner*—James S Ketter
(74) *Attorney, Agent, or Firm*—Robins & Pasternak LLP

(57) ABSTRACT

Accessory functions capable of supporting efficient recombinant AAV (rAAV) virion production in a suitable host cell are provided. The accessory functions are in the form of one or more vectors that are capable of being transferred between cells. Methods of producing rAAV virions are also provided. The methods can be practiced to produce commercially significant levels of rAAV particles without also generating significant levels of infectious helper virus or other contaminating by-products.

27 Claims, 3 Drawing Sheets

OTHER PUBLICATIONS

Richardson, et al., "A Cascade of Adenovirus Early Functions is Required for Expression of Adeno-Associated Virus," Cell 27(2):133-141 (1981).

Rolling, et al., "AAV as a Viral Vector for Human Gene Therapy," Molecular Biotechnology 3:9-15 (1995).

Samulski, et al., "Helper-Free Stocks of Recombinant Adeno-Associated Viruses: Normal Integration Does Not Require Viral Gene Expression," Journal of Virology 3822-3828 (1989).

Scaria, et al., "Complementation of a Human Adenovirus Early Region 4 Deletion Mutant in 293 Cells Using Adenovirus-Polylysine-DNA Complexes," Gene Therapy 2(4):295-298 (1995).

Schlehofer, et al., "Vaccinia Virus, Herpes Simplex Virus, and Carcinogens Induce DNA Amplification in a Human Cell Line and Support Replication of a Helpervirus Dependant Parvovirus," Virology 152:110-117 (1986).

Straus, et al., "DNA-Minus Temperature-Sensitive Mutants of Adenovirus Type 5 Help Adinovirus-Associated Virus Replication," J. Virology 14:140-148 (1976).

Wang, et al., "A Packaging Cell Line for Propagation of Recombinant Adenovirus Vectors Containing Two Lethal Gene-Region Deletions," Gene Therapy 2:775-783 (1995).

Weindler, et al., "A Subset of Herpes Simplex Virus Replication Genes Provides Helper Functions for Productive Adeno-Associated Virus Replication," J. Virology 65(5):2476-2483 (1991).

Weiss, et al., "Human Adenovirus Early Region 4 Open Reading Frame 1 Genes Encode Growth-Transforming Proteins That May Be Distinctly Related to dUTP Pyrophosphatase Enzymes," Journal of Virology 71(3):1857-1870 (1997).

Xiao, et al., "Production of High-Titer Recombinant Adeno-Associated Virus Vectors in the Absence of Helper Adenovirus," Journal of Virology 72(3):2224-2232 (1998).

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 14 base pairs
      (B) TYPE: nucleic acid (C) STRANDEDNESS: single
            (D) TOPOLOGY: linear (ii) MOLECULE TYPE: DNA (genomic)

(xi) SEQUENCE DESCRIPTION: SEQ ID NO: 1:

GGCAGCTGCC TGCA                                                           14

(2) INFORMATION FOR SEQ ID NO: 2:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 2:

GAAGGCGCGC CTTC                                                           14

(2) INFORMATION FOR SEQ ID NO: 3:

(i) SEQUENCE CHARACTERISTICS:
            (A) LENGTH: 80 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 3:

GCGGCCGCAC GCGTACGTAC CGGTTCGAAG CGCGCACGGC CGACCATGGT TAACTCCGGA          60

CACGTGCGGA CCGCGGCCGC                                                     80

(2) INFORMATION FOR SEQ ID NO: 4:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 4:

AAAATTCGAA CCTGGGGAGA AACCAGAG                                            28

(2) INFORMATION FOR SEQ ID NO: 5:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 5:

GTTTCCCCGC GAATGGACAA GCTTAAAA                                            28

(2) INFORMATION FOR SEQ ID NO: 6:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 6:

TTGCGGCCGC AA                                                              12

(2) INFORMATION FOR SEQ ID NO: 7:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 7:

GAAGGCGCGC CTTC                                                            14

(2) INFORMATION FOR SEQ ID NO: 8:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 8:

GAAGGCGCGC CTTC                                                            14

(2) INFORMATION FOR SEQ ID NO: 9:

(i) SEQUENCE CHARACTERISTICS:
      (A) LENGTH: 14 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 9:

GAAGGCGCGC CTTC                                                            14

(2) INFORMATION FOR SEQ ID NO: 10:

(i) SEQUENCE CHARACTERISTICS:
      (A) LENGTH: 33 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 10:

GTCGACAAAT CTAGATATCG CCCGGGCGGA TCC                                       33

(2) INFORMATION FOR SEQ ID NO: 11:

(i) SEQUENCE CHARACTERISTICS:
      (A) LENGTH: 95 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 11:

```
GCGGCCGCAC GCGTGAGCTC CGCGGTTCGA AGCGCGCAAA GCCCGGGCAA AGCGCGCAGA    60

TCTACGTAGG TAACCACGTG CGGACCGGCG GCCGC                              95
```

(2) INFORMATION FOR SEQ ID NO: 12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 12:

```
AAAATTCGAA CAGGTAAGCG CCCCTTTG                                      28
```

(2) INFORMATION FOR SEQ ID NO: 13:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 13:

```
GAGACCAAAG AGGGGTCCTA AGCTTAAAA                                     29
```

(2) INFORMATION FOR SEQ ID NO: 14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 14:

```
CCGCTACAGG GCGCGATATC AGCTCACTCA A                                  31
```

(2) INFORMATION FOR SEQ ID NO: 15:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

```
GGATCCGGTA CCGCCCGGGC TCTAGAATCG ATGTATACGT CGACGTTTAA ACCATATG     58
```

(2) INFORMATION FOR SEQ ID NO: 16:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 16:

```
AGAGGCCCGG GCGTTTTAGG GCGGAGTAAC TTGC                               34
```

```
(2) INFORMATION FOR SEQ ID NO: 17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

ACATACCCGC AGGCGTAGAG AC                                                22
```

US 7,485,458 B2

ACCESSORY FUNCTIONS FOR USE IN RECOMBINANT AAV VIRION PRODUCTION

CROSS-REFERENCE TO RELATED APPLICATION

This application is a continuation of U.S. patent application Ser. No. 10/177,871, filed Jun. 19, 2002 which is a divisional of U.S. patent application Ser. No. 09/406,363, filed Sep. 28, 1999, which is a continuation of U.S. patent application Ser. No. 08/745,957, filed Nov. 7, 1996, now U.S. Pat. No. 6,004,797, from which applications priority is claimed under to 35 USC §120, which claims the benefit of provisional patent application Ser. No. 60/006,402, filed Nov. 9, 1995, from which priority is claimed under 35 USC §119 (e)(1) and which applications are incorporated herein by reference in their entireties.

TECHNICAL FIELD

The present invention relates generally to accessory functions for use in adeno-associated virus (AAV) virion production. More particularly, the invention relates to vectors which provide accessory functions capable of supporting efficient recombinant AAV virion production in a suitable host cell, and methods of use thereof.

BACKGROUND OF THE INVENTION

Gene delivery is a promising method for the treatment of acquired and inherited diseases. A number of viral based systems for gene transfer purposes have been described, such as retroviral systems which are currently the most widely used viral vector systems for this purpose. For descriptions of various retroviral systems, see, e.g., U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Adeno-associated virus (AAV) systems have also been used for gene delivery. AAV is a helper-dependent DNA parvovirus which belongs to the genus Dependovirus. AAV requires infection with an unrelated helper virus, either adenovirus, a herpesvirus or vaccinia, in order for a productive infection to occur. The helper virus supplies accessory functions that are necessary for most steps in AAV replication. In the absence of such infection, AAV establishes a latent state by insertion of its genome into a host cell chromosome. Subsequent infection by a helper virus rescues the integrated copy which can then replicate to produce infectious viral progeny. AAV has a wide host range and is able to replicate in cells from any species so long as there is also a successful infection of such cells with a suitable helper virus. Thus, for example, human AAV will replicate in canine cells co-infected with a canine adenovirus. AAV has not been associated with any human or animal disease and does not appear to alter the biological properties of the host cell upon integration. For a review of AAV, see, e.g., Berns and Bohenzky (1987) Advances in Virus Research (Academic Press, Inc.) 32:243-307.

The AAV genome is composed of a linear, single-stranded DNA molecule which contains 4681 bases (Berns and Bohenzky, supra). The genome includes inverted terminal repeats (ITRs) at each end which function in cis as origins of DNA replication and as packaging signals for the virus. The ITRs are approximately 145 bp in length. The internal nonrepeated portion of the genome includes two large open reading frames, known as the AAV rep and cap regions, respectively. These regions code for the viral proteins involved in replication and packaging of the virion. In particular, a family of at least four viral proteins are synthesized from the AAV rep region, Rep 78, Rep 68, Rep 52 and Rep 40, named according to their apparent molecular weight. The AAV cap region encodes at least three proteins, VP1, VP2 and VP3. For a detailed description of the AAV genome, see, e.g., Muzyczka, N. (1992) Current Topics in Microbiol. and Immunol. 158: 97-129.

The construction of recombinant AAV virions has been described. See, e.g., U.S. Pat. Nos. 5,173,414 and 5,139,941; International Publication Numbers WO 92/01070 (published 23 Jan. 1992) and WO 93/03769 (published 4 Mar. 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; and Kotin, R. M. (1994) Human Gene Therapy 5:793-801.

Contemporary recombinant AAV (rAAV) virion production involves co-transfection of a host cell with an AAV vector plasmid and a construct which provides AAV helper functions to complement functions missing from the AAV vector plasmid. In this manner, the host cell is capable of expressing the AAV proteins necessary for AAV replication and packaging. The host cell is then infected with a helper virus to provide accessory functions. The helper virus is generally an infectious adenovirus (type 2 or 5), or herpesvirus.

AAV helper functions can be provided via an AAV helper plasmid that includes the AAV rep and/or cap coding regions but which lacks the AAV ITRs. Accordingly, the helper plasmid can neither replicate nor package itself. A number of vectors that contain the rep coding region are known, including those vectors described in U.S. Pat. No. 5,139,941, having ATCC Accession Numbers 53222, 53223, 53224, 53225 and 53226. Similarly, methods of obtaining vectors containing the HHV-6 homologue of AAV rep are described in Thomson et al. (1994) Virology 204:304-311. A number of vectors containing the cap coding region have also been described, including those vectors described in U.S. Pat. No. 5,139,941.

AAV vector plasmids can be engineered to contain a functionally relevant nucleotide sequence of interest (e.g., a selected gene, antisense nucleic acid molecule, ribozyme, or the like) that is flanked by AAV ITRs which provide for AAV replication and packaging functions. After an AAV helper plasmid and an AAV vector plasmid bearing the nucleotide sequence are introduced into the host cell by transient transfection, the transfected cells can be infected with a helper virus, most typically an adenovirus, which, among other functions, transactivates the AAV promoters present on the helper plasmid that direct the transcription and translation of AAV rep and cap regions. Upon subsequent culture of the host cells, rAAV virions (harboring the nucleotide sequence of interest) and helper virus particles are produced.

When the host cell is harvested and a crude extract is produced, the resulting preparation will contain, among other components, approximately equal numbers of rAAV virion particles and infectious helper virions. rAAV virion particles can be purified away from most of the contaminating helper virus, unassembled viral proteins (from the helper virus and AAV capsid) and host cell proteins using known techniques. Purified rAAV virion preparations that have been produced using infection with adenovirus type-2 contain high levels of contaminants. Particularly, 50% or greater of the total protein obtained in such rAAV virion preparations is free adenovirus fiber protein. Varying amounts of several unidentified adenoviral and host cell proteins are also present. Additionally, significant levels of infectious adenovirus virions are obtained, necessitating heat inactivation. The contaminating infectious adenovirus can be inactivated by heat treatment (56° C. for 1 hour) and rendered undetectable by sensitive adenovirus growth assays (e.g., by cytopathic effect (CPE) in a permissive cell line). However, heat treatment also results in an approximately 50 drop in the titer of functional rAAV virions.

Production of rAAV virions using an infectious helper virus (such as an adenovirus type-2, or a herpesvirus) to supply accessory functions is undesirable for several reasons. AAV vector production methods which employ a helper virus require the use and manipulation of large amounts of high titer infectious helper virus which presents a number of health and safety concerns, particularly in regard to the use of a herpesvirus. Also, concomitant production of helper virus particles in rAAV virion producing cells diverts large amounts of cellular resources away from rAAV virion production, possibly resulting in lower rAAV virion yields.

More particularly, in methods where infection of cells with adenovirus type-2 are used to provide the accessory functions, more than 95% of the contaminants found in the purified rAAV virion preparations are derived from adenovirus. The major contaminant, free adenovirus fiber protein, tends to co-purify with rAAV virions on CsCl density gradients due to a non-covalent association between the protein and rAAV virions. This association makes separation of the two especially difficult, lowering rAAV virion purification efficiency. Such contaminants may be particularly problematic since many adenoviral proteins, including the fiber protein, have been shown to be cytotoxic (usually at high concentrations), and thus may adversely affect or kill target cells. Thus, a method of producing rAAV virions without the use of infectious helper viruses to provide necessary accessory functions would be advantageous.

A number of researchers have investigated the genetic basis of accessory functions, particularly adenovirus-derived functions. Generally, two approaches have been used to attempt to identify those adenoviral genes that are involved in AAV replication: examination of the ability of various adenovirus mutants to provide accessory functions; and the study of the effect of transfected adenoviral genes or regions on AAV replication in the absence of adenovirus infection.

Studies with various adenovirus mutants that are capable of supporting AAV replication (e.g., by supplying necessary accessory functions) at or about the levels obtained by infection with a wild-type adenovirus have demonstrated that particular adenovirus genes or gene regions are not involved in AAV replication. However, loss-of-function data from such studies have failed to provide conclusive information that a particular gene region is involved with AAV replication since many of the adenovirus genes and control regions are overlapping and/or incompletely mapped.

Particularly, adenovirus mutants with fairly well characterized mutations in the following genes or gene regions have been tested for their ability to provide accessory functions necessary for AAV viral replication: E1a (Laughlin et al. (1982) *J. Virol.* 41:868, Janik et al. (1981) *Proc. Natl. Acad. Sci. USA* 78:1925); E1b (Laughlin et al. (1982), supra, Janik et al. (1981), supra, Ostrove et al. (1980) *Virology* 104:502); E2a (Handa et al. (1975) *J. Gen. Virol.* 29:239, Straus et al. (1976) *J. Virol.* 17:140, Myers et al. (1980) *J. Virol.* 35:665, Jay et al. (1981) *Proc. Natl. Acad. Sci. USA* 78:2927, Myers et al. (1981) *J. Biol. Chem.* 256:567); E2b (Carter, B. J. (1990) "Adeno-Associated Virus Helper Functions," in *CRC Handbook of Parvoviruses*, vol. I (P. Tijssen, ed.); E3 (Carter et al. (1983) *Virology* 126:505); and E4 (Carter et al. (1983), supra, Carter, B. J. (1995), supra). Poorly characterized adenovirus mutants that were incapable of DNA replication and late gene synthesis have also been tested (Ito et al. (1970) *J. Gen. Virol.* 9:243, Ishibashi et al. (1971) *Virology* 45:317).

Adenovirus mutants with defects in the E2b and E3 regions have been shown to support AAV replication, indicating that the E2b and E3 regions are probably not involved in providing accessory functions (Carter et al. (1983), supra). Mutant adenoviruses defective in the E1a region, or having a deleted E4 region, are unable to support AAV replication, indicating that the E1a and E4 regions are likely required for AAV replication, either directly or indirectly (Laughlin et al. (1982), supra, Janik et al. (1981), supra, Carter et al. (1983), supra). Studies with E1b and E2a mutants have produced conflicting results. Further, adenovirus mutants incapable of DNA replication and late gene synthesis have been shown to be permissive for AAV replication (Ito et al. (1970), supra, Ishibashi et al (1971), supra). These results indicate that neither adenoviral DNA replication nor adenoviral late genes are required for AAV replication.

Transfection studies with selected adenoviral genes have been used in an attempt to establish whether a transfected set of adenovirus genes is capable of providing the same level of accessory functions for AAV replication as that provided by an adenovirus infection. Particularly, in vitro AAV replication has been assessed using human 293 cells transiently transfected with various combinations of adenovirus restriction fragments encoding single adenovirus genes or groups of genes (Janik et al. (1981), supra). Since the above-described transfection studies were done in cells that stably express the adenovirus E1a and E1b regions, the requirement for those regions could not be tested. However, it was deduced that the combination of three adenoviral gene regions, VA I RNA, E2a and E4, could provide accessory functions (e.g., support AAV replication) at a level that was substantially above background, but that was still approximately 8,000 fold below the level provided by infection with adenovirus. When all combinations of two of the three genes were tested, the accessory function levels ranged between 10,000 to 100,000 fold below the levels provided by infection with adenovirus.

Transfection studies with selected herpes simplex virus type-1 (HSV-1) genes have also been conducted in an attempt to establish whether a transfected set of HSV-1 genes is capable of providing the same level of accessory functions for AAV replication as that provided by an HSV-1 infection. Weindler et al. (1991) *J. Virol.* 65:2476-2483. However, such studies were limited to identifying only those HSV-1 genes necessary to support wild-type AAV replication, not rAAV production. Further, the identified HSV-1 accessory functions were significantly less efficient at supporting AAV replication than adenovirus-derived functions.

Accordingly, there remains a need in the art to identify a subset of the adenovirus genome or functional homologues of the adenovirus genome, that include only those accessory functions required for rAAV virion production. The subset can then be included in an accessory function vector or system which, when introduced into a suitable host cell, supports the production of rAAV virions in an amount that is substantially equivalent to, or greater than, the amount produced using an adenovirus infection. Further, there remains a need to provide an accessory function system that is capable of producing commercially significant levels of rAAV virion particles without also generating significant levels of infectious adenovirus virions, or other contaminating by-products.

SUMMARY OF THE INVENTION

The present invention is based on the identification of the accessory functions needed to support efficient AAV replication in a suitable host cell. The invention provides a system which includes such functions and allows for the production of rAAV virions without the use of a helper virus.

In certain embodiments, the invention relates to nucleic acid molecules encoding accessory functions and that lack at least one adenoviral late gene region. The molecules can be provided in one or more vectors which include nucleotide sequences derived from an adenovirus type-2 or type-5 genome, or functional homologues thereof. Thus, in one aspect, the invention relates to a vector containing a nucleotide sequence selected from the group consisting of (i) a sequence that provides adenovirus VA RNAs, (ii) an adenovirus E4 ORFG coding region, (iii) an adenovirus E2a 72 kD coding region (coding for the E2a 72 kD DNA-binding protein), and any combination of nucleotide sequences (i), (ii) and (iii).

In another embodiment, the invention relates to nucleic acid molecules which provide accessory functions capable of supporting efficient recombinant AAV (rAAV) virion production in a suitable host cell and that lack at least one adenoviral late gene region and vectors containing the nucleic acid molecules.

In another aspect, the invention relates to a vector containing a plurality of nucleotide sequences, including a sequence that provides an adenovirus VA RNA, a sequence comprising an adenovirus E4 coding region and a sequence comprising an adenovirus E2a coding region.

In yet another aspect of the invention, a vector is provided which contains a sequence that provides an adenovirus VA RNA, a sequence comprising an adenovirus E4 coding region, a sequence comprising an adenovirus E2a coding region, and a sequence comprising an adenovirus E1a and E1b coding region.

In another embodiment of the invention, accessory function systems for rAAV virion production are provided, wherein the systems contain a plurality of accessory function vectors which provide accessory function components suitable for supporting efficient AAV virion production in a suitable host cell.

In yet another embodiment of the invention, methods for producing rAAV virions are provided. The methods generally entail (1) introducing an AAV vector into a suitable host cell; (2) introducing an AAV helper construct into the cell, wherein the helper. construct is capable of being expressed in the host cell to complement AAV helper functions missing from the AAV vector; (3) introducing one or more accessory function vectors into the host cell, wherein the one or more accessory function vectors provide accessory functions capable of supporting efficient rAAV virion production in the host cell; and (4) culturing the cell to produce rAAV virions.

In a further embodiment, recombinant AAV virions produced by the methods of the present invention are also provided.

These and other embodiments of the subject invention will readily occur to those of ordinary skill in the art in view of the disclosure herein.

DETAILED DESCRIPTION OF THE INVENTION

Figure 1:
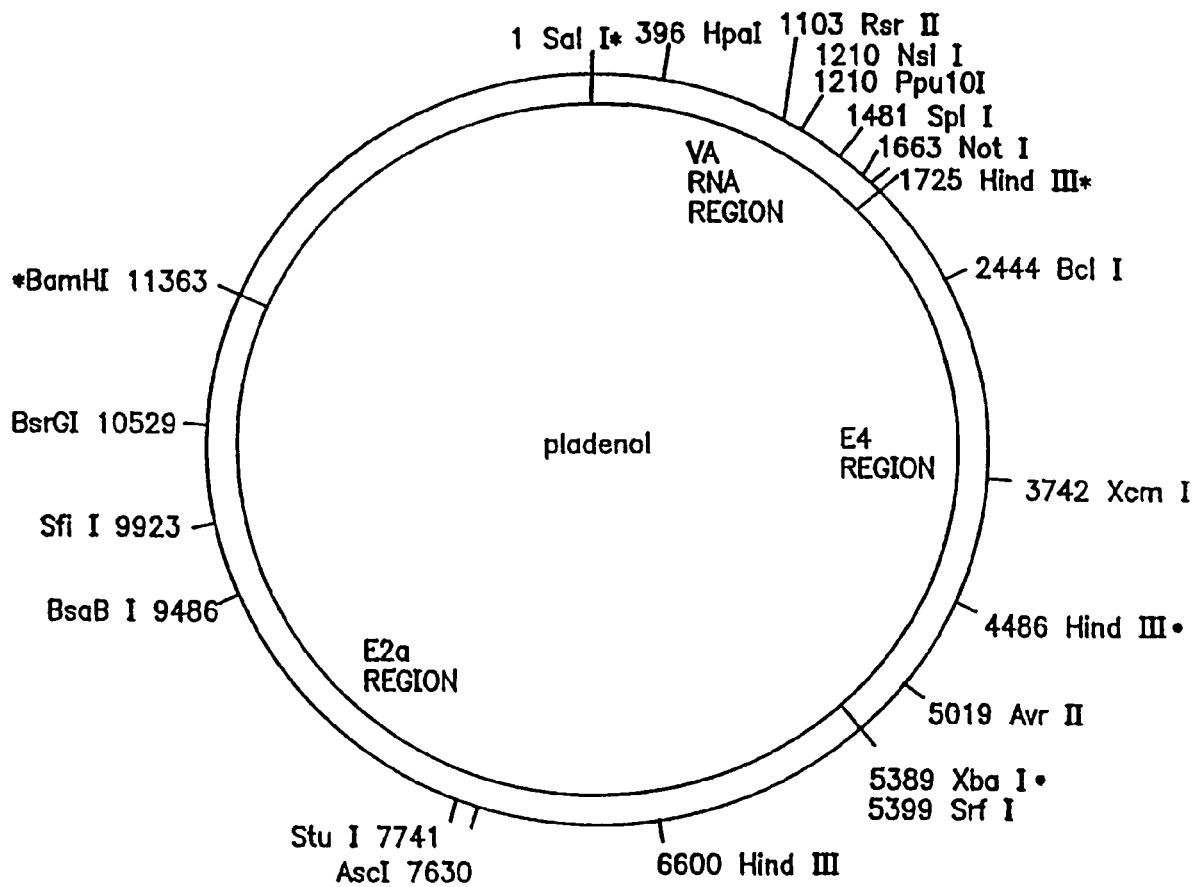
FIG. 1 depicts the plasmid construct pladeno 1 which includes VA RNA, E4 (containing the ORF 6) and E2a adenoviral gene regions derived from adenovirus type-5 which were inserted into a pBSII s/k− vector plasmid.

The practice of the present invention will employ, unless otherwise indicated, conventional methods of virology, microbiology, molecular biology and recombinant DNA techniques within the skill of the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *CRC Handbook of Parvoviruses*, vol. I & II (P. Tijessen, ed.); *Fundamental Virology*, 2nd Edition, vol. I & II (B. N. Fields and D. M. Knipe, eds.)

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

"Gene transfer" or "gene delivery" refers to methods or systems for reliably inserting foreign DNA into host cells. Such methods can result in transient expression of non-integrated transferred DNA, extrachromosomal replication and expression of transferred replicons (e.g., episomes), or integration of transferred genetic material into the genomic DNA of host cells. Gene transfer provides a unique approach for the treatment of acquired and inherited diseases. A number of systems have been developed for gene transfer into mammalian cells. See, e.g., U.S. Pat. No. 5,399,346.

By "vector" is meant any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

By "adeno-associated virus inverted terminal repeats" or "AAV ITRs" is meant the art-recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, e.g., Kotin, R. M. (1994) *Human Gene Therapy* 5:793-801; Berns, K. I. "Parvoviridae and their Replication" in *Fundamental Virology*, 2nd Edition, (B. N. Fields and D. M. Knipe, eds.) for the AAV-2 sequence. As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV-1, AAV-2, AAV-3, AAV-4, AAV-5, AAVX7, etc. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

By "AAV rep coding region" is meant the art-recognized region of the AAV genome which encodes the replication proteins of the virus which are collectively required for replicating the viral genome and for insertion of the viral genome into a host genome during latent infection, or functional homologues thereof such as the human herpesvirus 6 (HHV-6) rep gene which is also known to mediate AAV-2 DNA replication (Thomson et al. (1994) *Virology* 204:304-311). Thus, the rep coding region includes at least the genes encoding for AAV Rep 78 and Rep 68 (the "long forms of Rep"), and Rep 52 and Rep 40 (the "short forms of Rep"), or functional homologues thereof. For a further description of the AAV rep coding region, see, e.g., Muzyczka, N. (1992) *Current Topics in Microbiol. and Immunol.* 158:97-129; and Kotin, R. M. (1994) *Human Gene Therapy* 5:793-801. The rep coding region, as used herein, can be derived from any viral serotype, such as the AAV serotypes described above. The region need not include all of the wild-type genes but may be altered, e.g., by the insertion, deletion or substitution of nucleotides, so long as the rep genes present provide for sufficient integration functions when expressed in a suitable recipient cell.

By "AAV cap coding region" is meant the art-recognized region of the AAV genome which encodes the coat proteins of the virus which are collectively required for packaging the viral genome. Thus, the cap coding region includes at least the genes encoding for the coat proteins VP1, VP2 and VP3. For a further description of the cap coding region, see, e.g., Muzyczka, N. (1992) *Current Topics in Microbiol. and Immunol.* 158:97-129; and Kotin, R. M. (1994) *Human Gene Therapy* 5:793-801. The AAV cap coding region, as used herein, can be derived from any AAV serotype, as described above. The region need not include all of the wild-type cap genes but may be altered, e.g., by the insertion, deletion or substitution of nucleotides, so long as the genes provide for sufficient packaging functions when present in a host cell along with an AAV vector.

By an "AAV vector" is meant a vector derived from an adeno-associated virus serotype, including without limitation, AAV-1, AAV-2, AAV-3, AAV-4, AAV-5, AAVX7, etc. AAV vectors can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV vector is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging.

"AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) *J. Virol.* 63:3822-3828; and McCarty et al. (1991) *J. Virol.* 65:2936-2945. A number of other vectors have been described which encode Rep and/or Cap expression products. See, e.g., U.S. Pat. No. 5,139,941.

The term "accessory functions" refers to non-AAV derived viral and/or cellular functions upon which AAV is dependent for its replication. Thus, the term captures proteins and RNAs that are required in AAV replication, including those moieties involved in activation of AAV gene transcription, stage specific AAV mRNA splicing, AAV DNA-replication, synthesis of Cap expression products and AAV capsid assembly. Viral-based accessory functions can be derived from any of the known helper viruses such as adenovirus, herpesvirus (other than herpes simplex virus type-1) and vaccinia virus.

For example, adenovirus-derived accessory functions have been widely studied, and a number of adenovirus genes involved in accessory functions have been identified and partially characterized. See, e.g., Carter, B. J. (1990) "Adeno-Associated Virus Helper Functions," in *CRC Handbook of Paarvoviruses*, vol. I (P. Tijssen, ed.), and Muzyczka, N. (1992) *Curr. Topics. Microbiol. and Immun.* 158:97-129. Specifically, early adenoviral gene regions E1a, E2a, E4, VAI RNA and, possibly, E1b are thought to participate in the accessory process. Janik et al. (1981) *Proc. Natl. Acad. Sci. USA* 78:1925-1929. Herpesvirus-derived accessory functions have been described. See, e.g., Young et al. (1979) *Prog. Med. Virol.* 25:113. Vaccinia virus-derived accessory functions have also been described. See, e.g., Carter, B. J. (1990), supra., Schlehofer et al. (1986) *Virology* 152:110-117.

The term "accessory function vector" refers generally to a nucleic acid molecule that includes nucleotide sequences providing accessory functions. An accessory function vector can be transfected into a suitable host cell, wherein the vector is then capable of supporting AAV virion production in the host cell. Expressly excluded from the term are infectious viral particles as they exist in nature, such as adenovirus, herpesvirus or vaccinia virus particles. Thus, accessory function vectors can be in the form of a plasmid, phage, transposon or cosmid.

By "capable of supporting efficient rAAV virion production" is meant the ability of an accessory function vector or system to provide accessory functions that are sufficient to complement rAAV virion production in a particular host cell at a level substantially equivalent to or greater than that which could be obtained upon infection of the host cell with an adenovirus helper virus. Thus, the ability of an accessory function vector or system to support efficient rAAV virion production can be determined by comparing rAAV virion titers obtained using the accessory vector or system with titers obtained using infection with an infectious adenovirus. More particularly, an accessory function vector or system supports efficient rAAV virion production substantially equivalent to, or greater than, that obtained using an infectious adenovirus when the amount of virions obtained from an equivalent number of host cells is not more than about 200 fold less than the amount obtained using adenovirus infection, more preferably not more than about 100 fold less, and most preferably equal to, or greater than, the amount obtained using adenovirus infection.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.

A "recombinant AAV virion," or "rAAV virion" is defined herein as an infectious, replication-defective virus composed of an AAV protein shell, encapsidating a heterologous nucleotide sequence of interest which is flanked on both sides by AAV ITRs. A rAAV virion is produced in a suitable host cell which has had an AAV vector, AAV helper functions and accessory functions introduced therein. In this manner, the host cell is rendered capable of encoding AAV polypeptides that are required for packaging the AAV vector (containing a recombinant nucleotide sequence of interest) into infectious recombinant virion particles for subsequent gene delivery.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) *Virology*, 52:456, Sambrook et al. (1989) *Molecular Cloning, a laboratory manual*, Cold Spring Harbor Laboratories, New York, Davis et al. (1986) *Basic Methods in Molecular Biology*, Elsevier, and Chu et al. (1981) *Gene* 13:197. Such techniques can be used to introduce one or more exogenous DNA moieties, such as a nucleotide integration vector and other nucleic acid molecules, into suitable host cells.

The term "host cell" denotes, for example, microorganisms, yeast cells, insect cells, and mammalian cells, that can be, or have been, used as recipients of an AAV helper construct, an AAV vector plasmid, an accessory function vector, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

As used herein, the term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

A "coding sequence" or a sequence which "encodes" a particular protein, is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, cDNA from prokaryotic or eukaryotic MRNA, genomic DNA sequences from prokaryotic or eukaryotic DNA, and even synthetic DNA sequences. A transcription termination sequence will usually be located 3' to the coding sequence.

A "nucleic acid" sequence refers to a DNA or RNA sequence. The term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-.D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term DNA "control sequences" refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell.

The term "promoter region" is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence.

"Operably linked" refers to an arrangement of elements wherein the components so described are configured so as to perform their usual function. Thus, control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

By "isolated" when referring to a nucleotide sequence, is meant that the indicated molecule is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties which do not deleteriously affect the basic characteristics of the composition.

For the purpose of describing the relative position of nucleotide sequences in a particular nucleic acid molecule throughout the instant application, such as when a particular nucleotide sequence is described as being situated "upstream," "downstream," "3'," or "5'" relative to another sequence, it is to be understood that it is the position of the sequences in the "sense" or "coding" strand of a DNA molecule that is being referred to as is conventional in the art.

"Homology" refers to the percent of identity between two polynucleotide or two polypeptide moieties. The correspondence between the sequence from one moiety to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which allow for the formation of stable duplexes between homologous regions, followed by digestion with single-stranded-specific nuclease(s), and size determination of the digested fragments. Two DNA, or two polypeptide sequences are "substantially homologous" to each other when at least about 80%, preferably at least about 90%, and most preferably at least about 95% of the nucleotides or amino acids match over a defined length of the molecules, as determined using the methods above.

A "functional homologue," or a "functional equivalent" of a given polypeptide includes molecules derived from the native polypeptide sequence, as well as recombinantly produced or chemically synthesized polypeptides which function in a manner similar to the reference molecule to achieve a desired result. Thus, a functional homologue of AAV Rep68 or Rep78 encompasses derivatives and analogues of those polypeptides—including any single or multiple amino acid additions, substitutions and/or deletions occurring internally or at the amino or carboxy termini thereof—so long as integration activity remains.

A "functional homologue," or a "functional equivalent" of a given adenoviral nucleotide region includes similar regions derived from a heterologous adenovirus serotype, nucleotide regions derived from another virus or from a cellular source, as well as recombinantly produced or chemically synthesized polynucleotides which function in a manner similar to the reference nucleotide region to achieve a desired result. Thus, a functional homologue of an adenoviral VA RNA gene region or an adenoviral E2a gene region encompasses derivatives and analogues of such gene regions—including any single or multiple nucleotide base additions, substitutions and/or deletions occurring within the regions, so long as the homologue retains the ability to provide its inherent accessory function to support AAV virion production at levels detectable above background.

B. General Methods

Central to the present invention is the development of accessory function systems which allow for the efficient production of rAAV virions in the absence of infection with a helper virus. Unlike prior production methods, accessory functions are provided by introducing one or more vectors, such as plasmids, which contain genes required for complementing rAAV virion production, into a host cell. In this manner, the present accessory function systems can support the production of commercially significant levels of rAAV virions without significant levels of contaminating helper virus particles, or other contaminating virus products (e.g., the adenoviral fiber protein). Efficient production of rAAV virions is achieved when rAAV virion yields are obtained at levels that are not lower than about 200 fold less than levels obtained when using adenovirus type-2 infection to provide the accessory functions.

The accessory functions are provided on one or more vectors. The vector(s) will include adenoviral-derived nucleotide sequences necessary for rAAV virion production. As explained further below, the sequences present on the accessory function construct(s) will be determined by the host cell used and can include E1a, E1b, E2a, E4 and VA RNA regions.

While not being bound by any particular theory, the accessory functions provided by the adenovirus E1b, E2a, and E4 early genes are thought to be required in AAV DNA replication. The accessory functions provided by the adenovirus E1b, E4 and VA RNA gene regions appear to participate in post-transcriptional or translational events in the AAV life cycle. In regard to the accessory functions provided by E4, only the E4 34 kD protein encoded by open reading frame 6 (ORF 6) of the E4 coding region is clearly required for AAV replication. The accessory functions provided by the adenovirus gene region E1a are thought to be required as modulators to activate transcription or expression of the other adenovirus gene regions, including E1b, E2a, E4 and VA RNA.

The accessory function vectors of the invention can alternatively include one or more polynucleotide homologues which replace the adenoviral gene sequences, so long as each homologue retains the ability to provide the accessory functions of the replaced adenoviral gene. Thus, homologous nucleotide sequences can be derived from another adenoviral serotype (e.g., adenovirus type-2), from another helper virus moiety (e.g. a herpesvirus or vaccinia virus), or can be derived from any other suitable source.

Further, accessory function vectors constructed according to the invention can be in the form of a plasmid, phage, transposon or cosmid. Alternatively, the vector can be in the form of one or more linearized DNA or RNA fragments which, when associated with the appropriate control elements and enzymes, can be transcribed or expressed in a host cell to provide accessory functions. All of the above-described vectors can be readily introduced into a suitable host cell using transfection techniques that are known in the art. Such transfection methods have been described, including calcium phosphate co-precipitation (Graham et al. (1973) *Virol.* 52:456-467), direct micro-injection into cultured cells (Capecchi, M. R. (1980) *Cell* 22:479-488), electroporation (Shigekawa et al. (1988) *BioTechniques* 6:742-751), liposome mediated gene transfer (Mannino et al. (1988) *BioTechniques* 6:682-690), lipid-mediated transfection (Felgner et al. (1987) *Proc. Natl. Acad. Sci. USA* 84:7413-7417), and nucleic acid delivery using high-velocity microprojectiles (Klein et al. (1987) *Nature* 327:70-73).

Accessory function vectors can be engineered using conventional recombinant techniques. Particularly, nucleic acid molecules can be readily assembled in any desired order by inserting one or more accessory function nucleotide sequences into a construct, such as by ligating restriction fragments into a cloning vector using polylinker oligonucleotides or the-like. The newly formed nucleic acid molecule can then be excised from the vector and placed in an appropriate expression construct using restriction enzymes or other techniques that are well known in the art.

Figure 2:
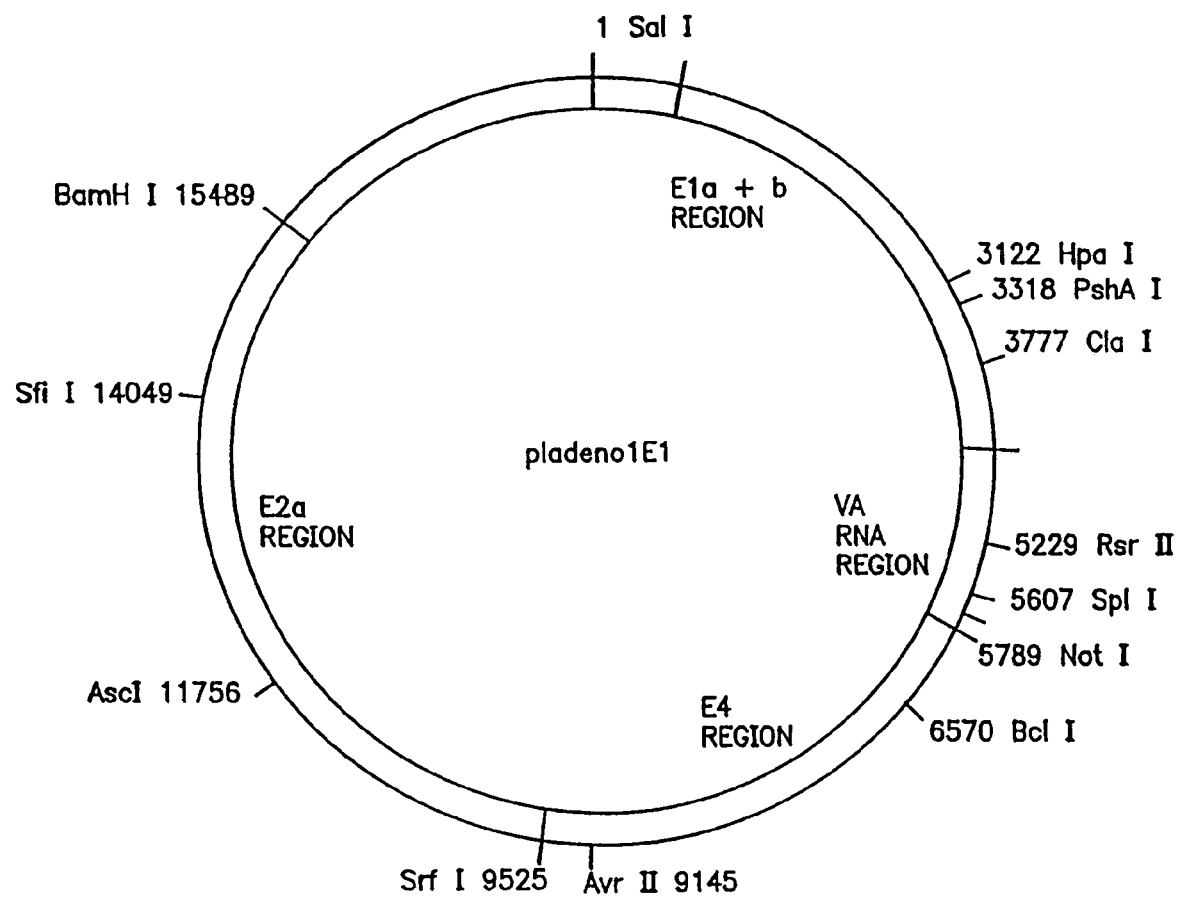
FIG. 2 depicts the plasmid construct pladeno 1 E1 which was formed by inserting a 4,102 bp BsxGI-Eco47III fragment (containing the adenovirus type-5 E1a and E1b coding regions) into the pladeno 1 construct.

More particularly, selected adenoviral genes or gene regions (e.g., E1a, E1b, E2a, E4 and VA RNA), or functional homologues thereof, can be excised from a viral genome, or from a vector containing the same, and inserted into a suitable vector either individually, or linked together, to provide an accessory function construct using standard ligation techniques such as those described in Sambrook et al., supra. Referring to FIG. 2, one such construct can be engineered to include four nucleic acid molecules derived from the adenovirus type-5 genome: a VA RNA-containing region; an E2a-containing region; an E4-containing region and an E1a, E1b-containing region. Specifically, FIG. 2 shows: a 1,724 bp SalI-HinDIII VA RNA-containing fragment (corresponding to the nucleotides spanning positions about 9,831 to about 11,555 of the adenovirus type-2 genome); a 5,962 bp SrfI-BamHI E2a-containing fragment (corresponding to the nucleotides spanning positions about 21,606 to about 27,568 of the adenovirus type-2 genome); a 3,669 bp HphI-HinDIII E4-containing fragment (corresponding to the nucleotides spanning positions about 32,172 to about 36,841 of the adenovirus type-2 genome); and a 4,102 bp BsrGI-Eco47III E1a-, E1b-containing fragment (corresponding to the nucleotides spanning positions about 192 to about 4294 of the adenovirus type-2 genome), wherein the nucleic acid molecules are ligated together to provide a complete complement of accessory functions in a single accessory function construct. Ligations can be accomplished in 20 mM Tris-Cl pH 7.5, 10 mM $MgCl_2$, 10 mM DTT, 33 ug/ml BSA, 10 mM-50 mM NaCl, and either 40 uM ATP, 0.01-0.02 (Weiss) units T4 DNA ligase at 0° C. (for "sticky end" ligation) or 1 mM ATP, 0.3-0.6 (weiss) units T4 DNA ligase at 14° C. (for "blunt end" ligation). Intermolecular "sticky end" ligations are usually performed at 30-100 µg/ml total DNA concentrations (5-100 nM total end concentration). The assembled molecule can then be readily inserted into an expression vector which is capable of transferring the accessory function construct between cells.

In the alternative, nucleic acid molecules comprising one or more accessory functions can be synthetically derived, using a combination of solid phase direct oligonucleotide synthesis chemistry and enzymatic ligation methods which are conventional in the art. Synthetic sequences may be constructed having features such as restriction enzyme sites, and can be prepared in commercially available oligonucleotide synthesis devices such as those devices available from Applied Biosystems, Inc. (Foster City, Calif.) using the phosphoramidite method. See, e.g., Beaucage et al. (1981) *Tetrahedron Lett.* 22:1859-1862. The nucleotide sequence of the adenovirus type-2 genome is generally known, and is publicly available (e.g., as GeneBank Reference Name: ADRCG, Accession Number: J01917; and as NCBI Identification Number: 209811). The nucleotide sequence of the adenovirus type-5 genome is believed to be 99% homologous to the adenovirus type-2 genome. Preferred codons for expression of the synthetic molecule in mammalian cells can also be readily synthesized. Complete nucleic acid molecules are then assembled from overlapping oligonucleotides prepared by the above methods. See, e.g., Edge, *Nature* (1981) 292:756; Nambair et al. *Science* (1984) 223:1299; Jay et al. *J. Biol. Chem.* (1984) 259:6311.

When adenoviral gene regions are used in the vectors of the invention to provide accessory functions, those regions will be operably linked to control sequences that direct the transcription or expression thereof. Such control sequences can comprise those adenoviral control sequences normally associated with the gene regions in the wild-type adenoviral genome. Alternatively, heterologpus control sequences can be employed where desired. Useful heterologous promoter sequences include those derived from sequences encoding mammalian genes or viral genes. Examples include, but are not limited to, homologous adenoviral promoters, the SV40 early promoter, mouse mammary tumor virus LTR promoter; adenovirus major late promoter (Ad MLP); a herpes simplex virus (HSV) promoter, a cytomegalovirus (CMV) promoter (e.g., the CMV immediate early promoter region), a rous sarcoma virus (RSV) promoter, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

Furthermore, the vectors of the present invention can be constructed to also include selectable markers. Suitable markers include genes which confer antibiotic resistance or sensitivity, or impart color, or change the antigenic characteristics when cells which have been transfected with the nucleic acid constructs are grown in an appropriate selective medium. Particular selectable marker genes useful in the practice of the invention include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

Accessory function vectors containing a full complement of the adenoviral accessory function genes or gene regions (e.g., E1a, E1b, E2a, E4, VA RNA, and/or functional homologues thereof) can be used to supply accessory functions to a host cell, including those cells not permissive for helper viruses (e.g., not infectable by a helper virus such as an adenovirus or not capable of supporting helper virus replication). In this manner, rAAV virion production can be carried out in a wide range of host cells, including those which were previously refractive to supporting such production.

In the alternative, accessory function vectors can be constructed to contain less than a full complement of accessory functions. Such vectors can be used in a cell that is already capable of supplying one or more accessory functions, for example, in a cell that supplies one or more accessory functions either inherently (e.g., where the cell expresses an accessory function homologue) or due to a transformation event. Accessory function vectors containing less than a full complement of accessory functions can also be used in combination with other ancillary accessory function constructs.

Particularly, suitable host cells can be engineered using ordinary recombinant techniques to produce cells that provide one or more accessory functions. For example, the human cell line 293 is a human embryonic kidney cell line that has been transformed with adenovirus type-5 DNA fragments (Graham et al. (1977) *J. Gen. Virol.* 36:59), and expresses the adenoviral E1a and E1b genes (Aiello et al. (1979) *Virology* 94:460). The 293 cell line is readily transfected, and provides a particularly convenient platform in which to produce rAAV virions. Thus, in one particularly preferred embodiment of the invention, an accessory function vector is provided having only the adenoviral E2a, E4 and VA RNA gene regions, or functional homologues thereof.

Referring to FIG. 1, one such construct can be engineered to include three nucleic acid molecules derived from the adenovirus type-5 genome: a 1,724 bp SalI-HinDIII VA RNA-containing fragment (corresponding to the nucleotides spanning positions about 9,831 to about 11,555 of the adenovirus-type-2 genome); a 5,962 bp SrfI-BamHI E2a-containing fragment (corresponding to the nucleotides spanning positions about 21,606 to about 27,568 of the adenovirus type-2 genome); and a 3,669 bp HphI-HinDIII E4-containing fragment (corresponding to the nucleotides spanning positions about 32,172 to about 36,841 of the adenovirus type-2 genome), wherein the nucleic acid molecules are ligated together to provide a truncated complement of accessory functions in a single accessory function construct.

Figure 3:
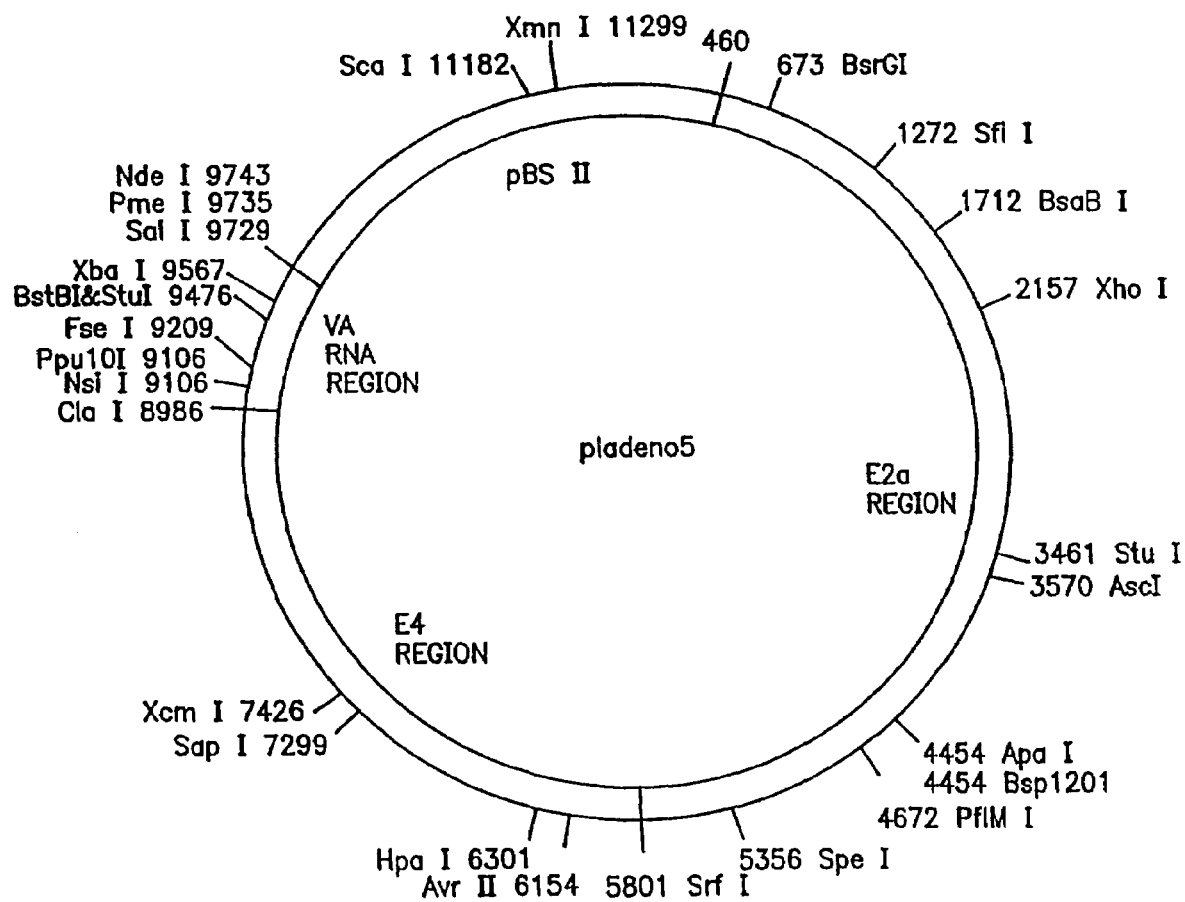
FIG. 3 depicts the plasmid construct pladeno 5 which includes the VA RNA, E4 ORF 6, and E2a adenoviral gene regions derived from the adenovirus type-2 genome.

Referring to FIG. 3, an alternative construct can be engineered to include three nucleic acid molecules derived from the adenovirus type-2 genome: a 732 bp EcoRV-SacII VA RNA-containing fragment (corresponding to the nucleotides spanning-positions about 10,423-11,155 of the adenovirus type-2 genome); a 5,962 bp SrfI-KpnI E2a-containing fragment (corresponding to the nucleotides spanning positions about 21,606 to about 27,568 of the adenovirus type-2 genome); and a 3,192 bp modified SrfI-SpeI E4 ORF6-containing fragment (corresponding to the nucleotides spanning positions about 32,644 to about 34,120 of the adenovirus type-2 genome. The nucleic acid molecules are ligated together to provide an even further truncated complement of accessory functions in a single accessory function construct.

These vectors can be constructed as described above using recombinant and/or synthetic techniques, and can include a variety of ancillary components such as heterologous promoter regions, selectable markers and the like. Upon transfection into a host 293 cell, the vectors provide accessory functions that are capable of supporting efficient rAAV virion production.

Once engineered, the accessory function vectors of the present invention can be used in a variety of systems for rAAV virion production. For example, suitable host cells that have been transfected with one or more accessory function vectors are thereby rendered capable of producing rAAV virions when co-transfected with an AAV vector and an AAV helper construct capable of being expressed in the cell to provide AAV helper functions.

The AAV vector, AAV helper construct and the accessory function vector(s) can be introduced into the host cell, either simultaneously or serially, using transfection techniques described above.

AAV vectors used to produce rAAV virions for delivery of a nucleotide sequence of interest can be constructed to include one or more heterologous nucleotide sequences flanked on both ends (5' and 3') with functional AAV ITRs. In the practice of the invention, an AAV vector generally includes at least one AAV ITR and an appropriate promoter sequence suitably positioned relative to a heterologous nucleotide sequence, and at least one AAV ITR positioned downstream of the heterologous sequence. The 5' and 3' ITRs need not necessarily be identical to, or derived from, the same AAV isolate, so long as they function as intended.

Suitable heterologous nucleotide sequences for use in AAV vectors include any functionally relevant nucleotide sequence. Thus, AAV vectors for use in the practice of the invention can include any desired gene that encodes a protein that is defective or missing from a recipient cell genome or that encodes a non-native protein having a desired biological or therapeutic effect (e.g., an antiviral function), or the sequence can correspond to a molecule having an antisense or ribozyme function. Suitable genes include, but are not limited to, those used for the treatment of inflammatory diseases, autoimmune, chronic and infectious diseases, including such disorders as AIDS, cancer, neurological diseases, cardiovascular disease, hypercholestemia; various blood disorders including various anemias, thalasemias and hemophilia; genetic defects such as cystic fibrosis, Gaucher's Disease, adenosine deaminase (ADA) deficiency, emphysema, or the like. A number of antisense oligonucleotides (e.g., short oligonucleotides complementary to sequences around the translational initiation site (AUG codon) of an mRNA) that are useful in antisense therapies for cancer, cardiovascular, and viral diseases have been described in the art. See, e.g., Han et al. (1991) *Proc. Natl. Acad. Sci. USA* 88:4313-4317; Uhlmann et al. (1990) *Chem. Rev.* 90:543-584; Helene et al. (1990) *Biochim. Biophys. Acta.* 1049:99-125; Agarwal et al. (1988) *Proc. Natl. Acad. Sci. USA* 85:7079-7083; and Heikkila et al. (1987) *Nature* 328:445-449. For a discussion of suitable ribozymes, see, e.g., Cech et al. (1992) *J. Biol. Chem.* 267:17479-17482 and U.S. Pat. No. 5,225,347 to Goldberg et al.

AAV vectors can also include control sequences, such as promoter and polyadenylation sites, as well as selectable markers or reporter genes, enhancer sequences, and other control elements which allow for the induction of transcription. Such AAV vectors can be constructed using techniques well known in the art. See, e.g., U.S. Pat. No. 5,173,414; International Publication Numbers WO 92/01070 (published 23 Jan. 1992) and WO 93/03769 (published 4 Mar. 1993); Lebkowski et al. (1988) *Molec. Cell. Biol.* 8:3988-3996; Vincent et al. (1990) *Vaccines* 90 (Cold Spring Harbor Laboratory Press); Carter, B. J. (1992) *Current Opinion in Biotechnology* 3:533-539; Muzyczka, N. (1992) *Current Topics in Microbiol. and Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

In the methods of the-invention, AAV helper constructs are used to complement AAV functions deleted from an AAV vector. A number of suitable AAV helper constructs have been described, including, e.g., the plasmids pAAV/Ad and pIM29+45 which encode both rep and cap expression products (see, e.g., Samulski et al. (1989) *J. Virol.* 63:3822-3828 and McCarty et al. (1991) *J. Virol.* 65:2936-2945). Complementing AAV helper functions in this manner to support rAAV virion production is an art-accepted technique. However, due to homologous recombination events between the AAV ITR sequences present in the AAV vector and the AAV helper function sequences present in the helper construct, such techniques also generate contaminating wild-type AAV virions in the rAAV virion stocks. The presence of wild-type AAV particles in AAV-based vector systems could potentially lead to unintentional spread of recombinant AAV virions, and may interfere with the efficient expression of foreign genes.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Plasmid Construction:

Plasmid JM17 (McGrory et al. (1988) *Virology* 163:614-617), which comprises a circularized isolate of adenovirus type-5 with the plasmid vector pBR322X inserted at the unique XbaI site at the end of the adenovirus E1a gene, was used as a source of adenovirus genes. Neither adenovirus type-5 nor pJM17 has been completely sequenced. Accordingly, the sizes of the adenovirus type-5 fragments described below have been approximated. Since adenovirus type-2 has been fully sequenced, and adenovirus types 2 and 5 are thought to be approximately 99% homologous, the adenovirus type-5 fragment sizes are approximated based upon corresponding adenovirus type-2 fragments.

Plasmid pBSII-VA RNAs (ATCC Accession Number 98233) was constructed as follows. The approximately 5,324 bp HinDIII-HinDIII fragment (containing the adenovirus type-5 VA RNA I and II-coding regions) was obtained from the plasmid pJM17. The 5,324 bp fragment was inserted into the plasmid vector pBSII s/k– (obtained from Stratagene) at the HinDIII site. The 5,324 bp fragment corresponds to the nucleotides extending from position 6,231 to 11,555 (HinDIII sites) of the adenovirus type-2 genome (publicly available, e.g., as GeneBank Reference Name: ADRCG, Accession Number: J01917; and NCBI Identification Number: 209811).

Plasmid pBSII-E2a+E4 was constructed as follows. The approximately 15,667 bp BamHI-XbaI fragment (containing the adenovirus type-5 E2a, E3 and E4 coding regions, adenoviral terminal repeats ligated head to head, and a portion of the adenovirus type-5 E1a coding region) was obtained from the plasmid pJM17. The plasmid vector pBSII s/k– was cut with BamHI and XbaI, and the 15,667 bp fragment was cloned into the subject vector. The 15,667 bp fragment corresponds to the nucleotides extending from position 21,606 (a BamHI site) to 35,937 (the distal end of the 3' terminus), and the nucleotides extending from position 1 (the beginning of the 5' terminus) to 1,336 (an XbaI site) of the adenovirus type-2 genome.

Plasmid pBSII-E2a was constructed as follows. The approximately 5,935 bp BamHI-EcoRI fragment (containing the adenovirus type-5 E2a coding region) was obtained from the plasmid pJM17. The plasmid vector PBSII s/k– was cut with BamHI and EcoRI, and the 5,935 bp fragment was cloned into the subject vector. The 5,935 bp fragment corresponds to the nucleotides extending from position 15,403 (a BamHI site) to 21,338 (an EcoRI site) of the adenovirus type-2 genome.

Plasmid pBSII-E4 was constructed as follows. The approximately 5,111 bp XhoI-XbaI fragment (containing the adenovirus type-5 E4 coding region, adenoviral terminal repeats ligated head to head, and a portion of the adenovirus type-5 E1 coding region) was obtained from pJM17. The plasmid vector pBSII s/k– was cut with XhoI and XbaI, and the 5,111 bp fragment was cloned into the subject vector. The 5,111 bp fragment corresponds to the nucleotides extending from position 29,788 (an XhoI site) to 35,937 (the end of the 3' terminus), and the nucleotides extending from position 1 (the beginning of the 5' terminus) to 1,336 (an XbaI site) of the adenovirus type-2 genome.

Plasmid pWadhlacZ was constructed as follows. The plasmid pUC119 (GeneBank Reference Name: U07649, GeneBank Accession Number: U07649) was partially digested with AflIII and BspHI, blunt-end modified with the klenow enzyme, and then ligated to form a circular 1732 bp plasmid containing the bacterial origin and the amp gene only (the polylinker and F1 origin was removed). The blunted and ligated AflIII and BspHI junction forms a unique NspI site. The 1732 bp plasmid was cut with NspI, blunt-end modified with T4 polymerase, and a 20 bp HinDIII-HinCII fragment (blunt-end modified with the klenow enzyme) obtained from the pUC119 polylinker was ligated into the blunted NspI site of the plasmid. The HinDIII site from the blunted polylinker was regenerated, and then positioned adjacent to the bacterial origin of replication. The resulting plasmid was then cut at the unique PstI/Sse8387I site, and an Sse8387I-PvuII-Sse8387I oligonucleotide (5'-GGCAGCTGCCTGCA-3' (SEQ ID NO:1)) was ligated in. The remaining unique BspHI site was cut, blunt-end modified with klenow enzyme, and an oligonucleotide containing an AscI linker (5'-GAAGGCGCGC-CTTC-3' (SEQ ID NO:2)) was ligated therein, eliminating the BspHI site. The resulting plasmid was called pWee.

In order to create the pWadhlacZ construct, a CMVlacZ expression cassette (comprising a nucleotide sequence flanked 5' and 3' by AAV ITRS, wherein the nucleotide sequence contains the following elements: a CMV promoter, the hGH 1st intron, an adhlacz fragment and an SV40 early polyadenylation site) was inserted into the unique PvuII site of pWee using multiple steps such that the CMV promoter was arranged proximal to the bacterial amp gene of pWee.

More particularly, a CMVlacZ expression cassette was derived from the plasmid psub201CMV, which was constructed as follows. An oligonucleotide encoding the restriction enzyme sites: NotI-MluI-SnaBI-AgeI-BstBI-BssHII-NcoI-HpaI-BspEI-PmlI-RsrII-NotI and having the following nucleotide sequence:

5'-GCGGCCGCACGCGTACGTACCGGTTC-
  GAAGCGCGCACGGCCGACCATGGT TAACTCCG-
  GACACGTGCGGACCGCGGCCGC-3' (SEQ ID NO:3)
was synthesized and cloned into the blunt-end modified KasI-EarI site (partial) of pUC119 to provide a 2757 bp vector fragment. A 653 bp SpeI-SacII fragment containing a nucleotide sequence encoding a CMV immediate early promoter was cloned into the SnaBI site of the 2757 bp vector fragment. Further, a 269 bp PCR-produced BstBI-BstBI fragment containing a nucleotide sequence encoding the hGH 1st intron which was derived using the following primers:

5'-AAAATTCGAACCTGGGGAGAAACCAGAG-3' (SEQ ID NO:4) and 3'-aaaattcgaacaggtaagcgcccctTTG-5' (SEQ ID NO:5), was cloned into the BstBI site of the 2757 bp vector fragment, and a 135 bp HpaI-BamHI (blunt-end modified) fragment containing the SV40 early polyadenylation site from the pCMV-β plasmid (obtained from Clonetech) was cloned into the HpaI site of the subject vector fragment to result in a plasmid called p1.1c. The p1.1c plasmid was then cut with NotI to provide a first CMV expression cassette.

The plasmid psub201 (Samulski et al. (1987) *J. Virol* 61:3096-3101) was cut with XbaI, blunt-end modified, and NotI linkers (5'-TTGCGGCCGCAA-3' (SEQ ID NO:6) were ligated to the ends to provide a vector fragment containing the bacterial origin of replication and an amp gene, wherein the vector fragment is flanked on both sides by NotI sites. After being cut with NotI, the first CMV expression cassette was cloned into the psub201 vector fragment to create psub201CMV. The ITR-bounded expression cassette from this plasmid was isolated by cutting with PvuII, and ligated to pWee after that plasmid was cut with PvuII to create pWCMV. pWCMV was then cut with BssHII (partial), and a 3246 bp fragment containing the adhlacZ gene (a SmaI-DraI nucleotide fragment obtained from the plasmid pCMV-β, having AscI linkers (5'-GAAGGCGCGCCTTC-3' (SEQ ID NO:7)) ligated to the ends to provide a 3246 bp fragment) was ligated into the BssHII site of pWCMV to obtain the pWadhlacZ construct.

Plasmid pW1909adhlacZ was constructed as follows. A 4723 bp SpeI-EcoRV fragment containing the AAV rep and cap encoding region was obtained from the plasmid pGN1909 (ATCC Accession Number 69871). The pGN1909 plasmid is a high efficiency AAV helper plasmid having AAV rep and cap genes with an AAV p5 promoter region that is arranged in the construct to be downstream from its normal position (in the wild type AAV genome) relative to the rep coding region. The 4723 bp fragment was blunt-end modified, and AscI linkers (5'-GAAGGCGCGCCTTC-3' (SEQ ID NO:8)) were ligated to the blunted ends. The resultant fragment was then ligated into the unique AscI site of pWadhlacZ and oriented such that the AAV coding sequences were arranged proximal to the bacterial origin of replication in the construct.

Plasmid pW620adhlacZ was constructed as follows. A 4439 bp MscI fragment containing the AAV rep and cap encoding region was obtained from the plasmid pSM620 (Samulski et al. (1982) *Proc. Natl. Acad. Sci. USA* 79:2077-2081. The 4439 bp fragment was blunt-end modified, and AscI linkers (5'-GAAGGCGCGCCTTC-3' (SEQ ID NO:9)) were ligated to the blunted ends. The resultant fragment was then ligated into the unique AscI site of pWadhlacZ and oriented such that the AAV coding sequences were arranged proximal to the bacterial origin of replication in the construct.

Plasmid pW1909 was constructed as follows. The pW1909adhLacZ plasmid was cut with Sse8387, and the 6506 bp Sse8387I-Sse8387I fragment (containing the ampicillin resistance gene, the coli 1 origin of replication, and the AAV helper sequence) was recircularized by intramolecular ligation to provide the pW1909 construct.

The pVlacZ vector plasmid is a modified version of the Sse8387I-Sse8371I fragment obtained from pW1909adhlacZ that has been cloned into the pUC119 plasmid. The Sse8387I-Sse8371I of pVlacZ differs from the Sse8387I-Sse8371I fragment of pW1909 in that all AAV sequences not derived from the AAV inverted terminal repeats (ITRs) have been eliminated. Plasmid pVlacZ was constructed as follows. Synthetic pieces of DNA, formed by combining AAV serotype 2 base pairs 122-145 with a downstream NotI compatible end, were constructed to provide MscI-NotI fragments containing AAV ITR sequences including all of the D loop. The synthetic DNAs were ligated onto both ends of the 4384 bp NotI fragment from the pW1909adhlacZ plasmid. The 4384 bp fragment contains the CMVlacZ sequences. The resulting fragment was then ligated into the 6732 bp MscI fragment of pW1909adhlacZ to provide an assembly construct. The assembly construct was cut with Sse8387I to obtain a 4666 bp Sse8387I-Sse8371I fragment (containing the CMVlacZ sequences) and the 4666 bp fragment was ligated into pUC119 at the Sse8387I site to obtain the pVlacZ vector plasmid.

EXAMPLE 1 rAAV Virion Production Using Transfected Adenovirus Genes to Supply Accessory Functions In order to determine whether adenoviral genes, introduced into a suitable host cell by transfection, are capable of providing accessory functions similar to those provided by an adenoviral infection in the context of AAV replication, the following experiment was conducted.

Cells from the stable human cell line, 293 (readily available through, e.g., the ATCC under Accession Number CRL1573), were plated in eight 10-cm tissue culture dishes at $1 \times 10^6$ cells/dish to provide 4 duplicate experimental groups. The cells were then grown at 37° C. to reach 90% confluency over a period of from about 24 to 48 hours prior to transfection. In each group, the plasmid pW1909adhlacZ was used as a source of rescuable AAVlacZ vector and AAV rep and cap coding regions.

Transfections were carried out using a modified calcium phosphate method with a total of 20 μg of DNA for a period of 5 hours. More particularly, at 1 to 4 hours prior to transfection, the medium in the tissue culture plates was replaced with fresh DME/F12 culture medium containing 10% FCS, 1% pen/strep and 1% glutamine. A total of 20 μg of DNA, comprising one or more vectors, was added to 1 mL of sterile 300 mM $CaCl_2$, which was then added to 1 mL of sterile 2× HBS solution (formed by mixing 280 mM NaCl, 50 mM HEPES buffer, 1.5 mM $Na_2HPO_4$ and adjusting the pH to 7.1 with 10 M NaOH) and immediately mixed by gentle inversion. The resultant mixture was pipetted immediately into the 10 cm plates of 90% confluent cells (in 10 mL of the above-described culture medium) and swirled to produce a homogeneous solution. The plates were transferred to a 5% $CO_2$ incubator and cultured at 37° C. for approximately 5 hours without disturbing. After transfection, the medium was removed from the plates, and the cells washed once with sterile Phosphate buffered saline (PBS).

Adenovirus working stock was prepared by diluting a master stock of adenovirus type-2 to a concentration of $10^6$ pfu/mL in DME/F12 plus 10% FCS, 1% pen/strep, 1% glutamine and 25 mM sterile HEPES buffer (pH 7.4).

Cell cultures from the first group were transfected with 10 μg each of the plasmids pW1909adhlacZ and pBSII s/k−. After the transfection period, the medium was replaced, 10 mL of medium containing adenovirus type-2 at a multiplicity of infection (moi) of 1 was added, and the cultures were incubated at 37° C. for approximately 72 hours.

Cell cultures from the second group were transfected with 10 μg each of the plasmids pW1909adhlacZ and pJM17. After the transfection period, the medium was replaced, and the cultures were incubated at 37° C. for approximately 72 hours.

Cell cultures from the third group were transfected with 10 μg each of pBSII s/k− and pJM17. After the transfection period, the medium was replaced, and the cultures were incubated at 37° C. for approximately 72 hours.

Cell cultures from the fourth group were transfected with 10 μg each of pW1909adhlacZ and pBSII s/k−. After the transfection period, the medium was replaced, and the cultures were incubated at 37° C. for approximately 72 hours.

The cells from each experimental group were then collected, media was removed by centrifugation (1000×g for 10 min.), and a 1 mL lysate was produced using 3 freeze/thaw cycles (alternating between dry ice-ethanol and 37° C. baths). The lysates were made free of debris by centrifugation (10,000×g for 10 min). rAAV lacZ virion production was assessed by titering the freeze/thaw extracts on 293 cells, and assaying for lacz.

Specifically, 293 cells were plated in 12 well plates (at $1 \times 10^5$ cells per well) and inoculated with a range of volumes (10-0.01 μL) of the above-described freeze/thaw lysates and incubated for 24 hours at 37° C. The cells were then fixed and stained by removal of the medium, incubation of the cells for 5 minutes in PBS containing 2% formaldehyde and 0.2% glutaraldehyde, washing once with PBS, and then incubating the cells over-night in PBS containing 5 mM potassium ferrocyanide, 5 mM potassium ferricyanide, 2 mM magnesium chloride, and 1 mg/ml X-Gal (Sanes et al. (1986) *EMBO* 5:3133-3142). The rAAV virion titer was then calculated by quantifying the number of blue cells using light microscopy.

Contaminating infectious adenovirus production was assayed as follows. Samples from the cell lysates were added to 50% confluent 293 cells (cultured in 12 well dishes at $1\times10^5$ cells/well), and the cultures were passaged for 30 days (e.g., the cultures were split 1 to 5, every 3 days) or until the culture exhibited 100% CPE due to adenovirus infection. Cultures were examined daily for CPE, and the day upon which each experimental culture showed 100% CPE was noted. Reference 293 cell cultures infected with a range of known amounts of adenovirus type-2 (from 0 to $1\times10^7$ pfu/culture) were also prepared and treated in the same manner. A standard curve was then prepared from the data obtained from the reference cultures, where the adenovirus pfu number was plotted against the day of 100% CPE. The titer of infectious adenovirus type-2 in each experimental culture was then readily obtained as determined from the standard curve. The limit of detection in the assay was 100 pfu/mL.

The results of the experiment are depicted below in Table 1.

TABLE 1

| Group | Transfected Plasmids | ad-2 Infection | rAAV Titer† | Adenovirus Titer |
|---|---|---|---|---|
| 1 | pW1909lacZ/pBS | yes | $1 \times 10^{10}$ | $\geq 10^9$ pfu/mL |
| 1 | pW1909lacZ/pBS | yes | $1 \times 10^{10}$ | $\geq 10^9$ pfu/mL |
| 2 | pW1909lacZ/pJM17 | no | $1 \times 10^9$ | none detected |
| 2 | pW1909lacZ/pJM17 | no | $2 \times 10^9$ | none detected |
| 3 | pBS/pJM17 | no | 0 | $10^4$ pfu/mL |
| 3 | pBS/pJM17 | no | 0 | $10^4$ pfu/mL |
| 4 | pW1909lacZ/pBS | no | 0 | not tested |
| 4 | pW1909lacZ/pBS | no | 0 | not tested |

†As determined by the lacZ assay.

As can be seen by the results in Table 1, adenoviral genes introduced into a host cell by transfection and expressed in the absence of adenoviral infection can provide accessory functions at a level that is approximately 20% (e.g., 5 fold less) as effective as the level of accessory functions provided by an adenovirus infection.

EXAMPLE 2

Identification of Adenoviral Gene Regions Responsible for Accessory Functions

In order to determine which adenoviral genes or gene regions are necessary and sufficient in the provision of accessory functions, the following experiment was conducted.

293 cells were plated in twelve 10-cm tissue culture dishes at $1\times10^6$ cells/dish to provide 6 duplicate experimental groups. The cells were then grown at 37° C. to reach approximately 90% confluency over a period of from about 24 to 48 hours prior to transfections. In each group, the plasmid pW1909adhlacZ was used as a source of rescuable AAVlacZ vector and AAV rep and cap coding regions. Transfections were carried out as described above in Example 1. Adenovirus working stock was also prepared as previously described.

Each of the 293 cell cultures were transfected with the plasmid pW1909adhlacZ and either the plasmid pBSII s/k– (as a control), or various combinations of isolated adenoviral genes.

More particularly, cells in the first experimental group were co-transfected with 5 μg of the plasmid pW1909adhlacZ (to provide AAV help functions) and 15 μg of the plasmid pBSII s/k–. After the transfection period, the medium was replaced, and the cells were infected using 10 mL medium containing adenovirus type-2 (moi=1). The cultures were then incubated at 37° C. for approximately 72 hours.

Cells in the second experimental group were co-transfected with 5 μg of the plasmid pW1909adhlacZ (to provide AAV help functions), and 15 μg of the plasmid pJM17. After the transfection, the medium was replaced and the cultures were incubated at 37° C. for approximately 72 hours.

Cells in the third experimental group were co-transfected with 5 μg of the plasmid pW1909adhlacZ (to provide AAV help functions), 10 μg of the plasmid pBSII-E2a+E4, and 5 μg of the plasmid pBSII s/k–. After the transfection, the medium was replaced, and the cultures were incubated at 37° C. for approximately 72 hours.

Cells in the fourth experimental group were co-transfected with 5 μg of the plasmid pW1909adhlacZ (to provide AAV help functions), 10 μg of the plasmid pBSII-E2a+E4, and 5 μg of the plasmid PBSII-VA RNAs. After the transfection, the medium was replaced, and the cultures were incubated at 37° C. for approximately 72 hours.

Cells in the fifth experimental group were co-transfected with 5 μg of the plasmid pW1909adhlacZ (to provide AAV help functions), 5 μg of the plasmid pBSII-E2a, 5 μg of the plasmid pBSII-E4, and 5 μg of the plasmid pBSII s/k–. After the transfection, the medium was replaced, and the cultures were incubated at 37° C. for approximately 72 hours.

Cells in the sixth experimental group were co-transfected with 5 μg of the plasmid pW1909adhlacZ (to provide AAV help functions), 5 μg of the plasmid pBSII-E2a, 5 μg of the plasmid pBSII-E4, and 5 μg of the plasmid PBSII-VA RNAs. After the transfection, the medium was replaced, and the cultures were incubated at 37° C. for approximately 72 hours.

The cells from each experimental group were then collected, media was removed by centrifugation (1000×g for 10 min.), and a 1 mL lysate was produced using 3 freeze/thaw cycles (alternating between dry ice-ethanol and 37° C. baths). The lysates were made free of debris by centrifugation (10,000×g for 10 min). rAAV lacZ virion production was then assessed using the techniques described in Example 1, and the amount of rAAV genomes was quantified by the following assay method.

50λ of the lysate from each experimental group was added to a 100λ aliquot of DMEM medium (available from Sigma, St. Louis, Mo.) containing 50 U/mL DNAse I to form assay samples. The samples were incubated at 37° C. for approximately 1 hour, after which 100λ of proteinase K (1 mg/mL) in a 2× proteinase K buffer (20 mM Tris Cl, 20 mM EDTA, 1% SDS, pH adjusted to 8.0) was added to each sample which were then incubated at 37° C. for another hour. DNA from the samples was phenol/chloroform extracted, precipitated in EtOH and then collected by centrifugation at 5° C. for 15 minutes. The DNA pellets were then redissolved in 200λ TE to provide DNA samples. Dot blot assays were then conducted as follows. Zeta probe® membrane (Bio Rad, Richmond, Calif.) was cut to size and assembled into a dot blot apparatus. The DNA samples were denatured using 200λ of a 2× alkaline solution (0.8 M NaOH, 20 mM EDTA), and, after 5 minutes, the membranes were rinsed in a 2×SSC solution for 1 minute, dried on filter paper, then baked under vacuum at 80° C. for approximately 30 minutes. Hybridizations were carried out at 65° C. for 30 minutes in hybridization buffer (1 mM EDTA, 40 mM $Na_2HPO_4$ (pH 7.2), 7% SDS). The filters were then washed and autoradiographed for approximately 20 hours, radioactivity was determined using scintillation counting.

The results from the experiment are depicted below in Table 2.

TABLE 2

| Group | Transfected Plasmids | ad-2 Infection | rAAV Titer† | Genomes/mL |
|---|---|---|---|---|
| 1 | pW1909lacZ | yes | $2 \times 10^9$ | $3 \times 10^{11}$ |
| 2 | pW1909lacZ, pJM17 | no | $2 \times 10^9$ | $4 \times 10^{11}$ |
| 3 | pW1909lacZ, pBSII-E2a + E4 | no | $4 \times 10^8$ | $1 \times 10^{11}$ |
| 4 | pW1909lacZ, pBSII-E2a + E4, pBSII-VA RNAs | no | $3 \times 10^9$ | $5 \times 10^{11}$ |
| 5 | pW1909lacZ, pBSII-E2a, pBSII-E4 | no | $2 \times 10^8$ | $1 \times 10^{11}$ |
| 6 | pW1909lacZ, pBSII-E2a, pBSII-E4, pBSII-VA RNAs | no | $2 \times 10^9$ | $4 \times 10^{11}$ |

†As determined by the lacZ assay.

As can be seen by the results depicted in Table 2, isolated adenoviral gene regions can be successfully transfected into host cells to provide accessory functions that are necessary and sufficient for rAAV virion replication. Further, the results obtained with groups 3 and 5 indicate that the adenoviral VA RNA region is not essential for the replication of rAAV virions; however, the region is needed to obtain rAAV titers comparable to those obtained using adenoviral infection.

EXAMPLE 3

Correlation of Adenoviral VA RNA Dosage to rAAV Virion Production

In order to investigate whether a correlation exists between the amount of transfected adenoviral VA RNA gene region supplied to a host cell, and the level of accessory functions provided to complement rAAV replication in the host cell, the following experiment was carried out.

293 cells were plated in 10-cm tissue culture dishes at $1 \times 10^6$ cells/dish, and were cultured at 37° C. to reach approximately 90% confluency over a period of from about 24 to 48 hours prior to transfections. Transfections were carried out as described above in Example 1.

Specifically, 293 cells were transfected with 5 µg of the plasmid pW1909adhlacZ, 10 µg of the plasmid pBSII-E2a+ E4 and from 0 to 25 µg of the plasmid pBSII-VA RNAs to vary the molar ratio of the VA RNA bearing plasmid (relative to the other plasmids) over the range of 0 to 5. After the transfection period, the medium was exchanged, and the cells were incubated at 37° C. for approximately 72 hours.

Cells from each experimental group were then collected, media was removed by centrifugation (1000×g for 10 min.), and a 1 mL lysate was produced using 3 freeze/thaw cycles (alternating between dry ice-ethanol and 37° C. baths). The lysates were made free of debris by centrifugation (10,000×g for 10 min). AAV lacZ vector production was then assessed using the techniques described in Example 1. The results from the experiment are depicted below in Table 3.

TABLE 3

| Amount of pBSII-VA RNAs Transfected (µg) | Molar Ratio of pBSII-VA RNAs/other plasmids | rAAV Titer† |
|---|---|---|
| 0 | 0 | $3 \times 10^8$ |
| 1 | 0.2 | $6 \times 10^9$ |
| 5 | 1 | $1 \times 10^{10}$ |
| 10 | 2 | $7 \times 10^9$ |
| 25 | 5 | $5 \times 10^9$ |

†As determined by the lacZ assay.

As can be seen from Table 3, although adenoviral VA RNAs are needed to obtain rAAV virion production at levels substantially equivalent to those obtained with adenoviral infection, variations in the ratio of VA RNA/other adenoviral gene regions over the range investigated does not significantly effect rAAV virion production.

EXAMPLE 4

Demonstration of the Requirement for Adenoviral E2a, E4 and VA RNA Gene Regions in Accessory Functions In order to establish the relative contributions of the adenoviral E2a, E4 and VA RNA gene regions in the provision of accessory functions for rAAV virion production, the following experiment was carried out.

293 cells were plated in 10-cm tissue culture dishes at $1 \times 10^6$ cells/dish, and were cultured at 37° C. to reach approximately 90% confluency over a period of from about 24 to 48 hours prior to co-transfections. All transfections were carried out as described above in Example 1.

The 293 cell cultures were co-transfected with 5 g of the plasmid pW1909adhlacZ, and 15 µg (total) of either all, or paired combinations of the following plasmids: pBSII-E2a; pBSII-E4; and pBSII-VA RNAs to provide cultures in which each of the adenoviral gene regions encoding E2a, E4 and VA RNA were eliminated from a co-transfection. After the transfection period, the media was replaced, and the cells were incubated at 37° C. for approximately 72 hours.

The cells from each co-transfection group were then collected, media was removed by centrifugation (1000×g for 10 min.), and a 1 mL lysate was produced-using 3 freeze/thaw cycles (alternating between dry ice-ethanol and 37° C. baths). The lysates were made free of debris by centrifugation (10, 000×g for 10 min). rAAV lacz virion production was then assessed using the techniques described in Example 1. The results from the experiment are depicted below in Table 4.

TABLE 4

| Co-transfection with Helper Plasmids Encoding | | | |
|---|---|---|---|
| E2a | E4 | VA RNAs | rAAV Titer† |
| + | + | + | $5 \times 10^9$ |
| − | + | + | $5 \times 10^5$ |
| + | − | + | $6 \times 10^7$ |
| + | + | − | $7 \times 10^8$ |
| − | − | − | 0 |

†As determined by the lacZ assay.

As can be seen by the results depicted in Table 4, each of the adenoviral gene regions E2a, E4 and VA RNA are not absolutely essential to provide the accessory functions needed to support rAAV virion production; however, all of the gene regions are needed to produce levels of rAAV virions comparable to those obtained with adenoviral infection. More particularly, omission of the VA RNA containing plasmid from the co-transfection resulted in a 7 fold drop in rAAV virion production (7×10⁸ functional units per 10 cm dish). rAAV virion production was even more severely affected by omission of the E4- and E2a-containing plasmids from the co-transfection. Omission of the E4 construct resulted in an 83 fold drop in production (6×10⁷ functional units per 10 cm dish), and omission of the E2 construct resulted in a 10,000 fold drop in rAAV virion production (5×10⁵ functional units per 10 cm dish).

EXAMPLE 5

Comparison of rAAV Virion Production Using PW1909adhlacZ or pW620adhlacZ Based AAV Help In order to compare the efficiency of rAAV virion production in a host cell using non-viral accessory function systems with AAV helper constructs containing either wild-type or modified AAV help functions (AAV rep and cap coding regions), the following experiment was carried out.

293 cells were plated in 10-cm tissue culture dishes at 1×10⁶ cells/dish, and were cultured at 37° C. to reach approximately 90% confluency over a period of from about 24 to 48 hours prior to co-transfections. All transfections were carried out as described above in Example 1.

A first set of 293 cell cultures was co-transfected with 5 μg of the plasmid pW620adhlacZ (containing wild-type AAV help functions), 10 μg of the plasmid pBSII-E2a+E4 and 5 μg of the plasmid pBSII-VA RNAs. A second set of 293 cultures was co-transfected with 5 μg of the plasmid pW1909adhlacZ (containing modified AAV help functions), 10 μg of the plasmid PBSII-E2a+E4 and 5 μg of the plasmid PBSII-VA RNAs. After the transfections, the media was replaced, and the cultures were incubated at 37° C. for approximately 72 hours.

Cells from each co-transfection group were then collected, media was removed by centrifugation (1000×g for 10 min.), and a 1 mL lysate was produced using 3 freeze/thaw cycles (alternating between dry ice-ethanol and 37° C. baths). The lysates were made free of debris by centrifugation (10,000×g for 10 min). rAAV lacZ virion production was then assessed using the techniques described in Example 1. The results from the experiment are depicted below in Table 5.

TABLE 5

| Vector/Helper Construct | rAAV Titer† |
|---|---|
| pW1909adhlacZ | 5 × 10⁹ |
| pW620adhlacZ | 4 × 10⁹ |

†As determined by the lacZ assay.

As can be seen from the results depicted in Table 5, both the wild-type and modified forms of AAV help supported rAAV virion production at approximately the same level.

EXAMPLE 6

Comparison of rAAV Virion Production Efficiency of Plasmid-Based Accessory Functions In order to compare the efficiency of rAAV virion production in a host cell using plasmid-based isolated accessory functions, combinations thereof, and a single construct containing adenovirus VA RNA, E4 and E2a gene regions (the pladeno 1 plasmid, described below) with rAAV virion production obtained using adenovirus type-2 (ad-2) infection, the following experiment was carried out.

1. Construction of pladeno 1 and pladeno 1 E1:

The plasmid pladeno 1, containing adenovirus VA RNA, E4 and E2a gene regions, was assembled by cloning adenovirus type-5 genes into a custom polylinker that was inserted between the PvuII sites of pBSII s/k–. A map of the pladeno 1 construct is depicted in FIG. 1. More particularly, a double stranded oligonucleotide polylinker encoding the restriction enzyme sites SalI-XbaI-EcoRV-SrfI-BamHI (5'-GTCGACAAATCTAGATATCGCCCGGGCGGATCC-3' (SEQ ID NO:10)) was ligated to the 2513 bp PvuII vector fragment of pBSII s/k– to provide an assembly plasmid. The following fragments containing adenovirus type-5 genes or gene regions were then obtained from the pJM17 plasmid: the 1,724 bp SalI-HinDIII VA RNA-containing fragment (corresponding to the nucleotides spanning positions about 9,831 to about 11,555 of the adenovirus type-2 genome); the 5,962 bp SrfI-BamHI E2a-containing fragment (corresponding to the nucleotides spanning positions about 21,606 to about 27,568 of the adenovirus type-2 genome); and the 3,669 bp HphI-HinDIII E4-containing fragment (corresponding to the nucleotides spanning positions about 32,172 to about 36,841 of the adenovirus type-2 genome). An XbaI site was added to the HphI end of the E4-containing fragment by cloning the 3,669 bp HphI-HinDIII fragment into the HpaI site of cloning vector, and then excising the fragment with XbaI and HinDIII (partial digestion). The 5,962 E2a-containing fragment was cloned between the SrfI and BamHI sites of the assembly plasmid, and the 1,724 bp VA RNA-containing fragment and the modified 3,669 bp E4-containing fragments were joined by their common HinDIII ends and ligated between the SalI and XbaI sites of the assembly plasmid to obtain the pladeno 1 construct.

Referring now to FIG. 2, the pladeno 1 E1 plasmid was assembled as follows. The 4,102 bp BsrGI-Eco47III fragment (containing the adenovirus type-5 E1a and E1b coding regions) was obtained from the pJM17 plasmid. The subject fragment corresponds to the nucleotides spanning positions about 192 to about 4,294 of the adenovirus type-2 genome. The 4,102 bp fragment was blunt-end modified, and then inserted into the HpaI site in the VA RNA fragment of the pladeno 1 plasmid to obtain the pladeno 1 E1 plasmid.

2. rAAV Virion Production Assay:

293 cells were plated in 10-cm tissue culture dishes at 1×10⁶ cells/dish, and were cultured at 37° C. to reach approximately 90% confluency over a period of from about 24 to 48 hours prior to co-transfections. All transfections were carried out as described above in Example 1.

All of the 293 cell cultures were transfected with 5 μg of the plasmid pW1909adhlacZ. Experimental groups of the cultures were also co-transfected with various combinations of 5 μg each of the accessory function containing plasmids or control plasmid (pBSII s/k–). After the transfections, the media was replaced, and the cultures were incubated at 37° C. for approximately 72 hours. As a comparison, 10 mL of medium containing adenovirus type-2 (moi=1) was added to 293 cells that had been transfected with 5 μg of the plasmid pW1909adhlacZ, and incubated at 37° C. for approximately 72 hours.

Cells from each experimental group were then collected, media was removed by centrifugation (1000×g for 10 min.), and a 1 mL lysate was produced using 3 freeze/thaw cycles (alternating between dry ice-ethanol and 37° C. baths). The lysates were made free of debris by centrifugation (10,000×g for 10 min). rAAV lacZ virion production was then assessed using the techniques described in Example 1. The results from the experiment are depicted below in Table 6.

TABLE 6

| Transfected Plasmids | AAV Titer† |
|---|---|
| ad-2 (moi = 1) | $5 \times 10^9$ |
| pladeno 1 | $3 \times 10^9$ |
| pBSII-E2a, pBSII-E4, pBSII-VA RNAs | $1 \times 10^9$ |
| pBSII-E2a + E4, pBSII-VA RNAs | $5 \times 10^8$ |
| pladeno 1, pBSII-E2a | $8 \times 10^9$ |
| pladeno 1, pBSII-E4 | $2 \times 10^9$ |
| pladeno 1, pBSII-VA RNAs | $2 \times 10^9$ |
| pladeno 1, pBSII-E2a + E4 | $1 \times 10^9$ |
| pBSII-E2a | $2 \times 10^7$ |
| pBSII-E4 | $<10^4$ |
| pBSII-VA RNAs | $3 \times 10^4$ |
| pBSII s/k– | $<10^4$ |

†As determined by the lacZ assay.

As can be seen by the results in Table 6, the pladeno 1 construct is capable of supporting efficient rAAV virion production (at substantially the same level as that obtained using adenovirus type-2 infection). The combination of accessory function constructs pBSII-E2a, pBSII-E4 and pBSII-VA RNAs was also able to support efficient rAAV virion production at levels substantially equivalent to ad-2 infection. The combination of accessory function constructs pBSII-E2a+E4 and pBSII-VA RNAs was able to support rAAV production (10 fold less than ad-2 infection levels); and the E2a containing construct (pBSII-E2a) supported rAAV production at a level approximately 200 fold less than that obtained using ad-2 infection.

EXAMPLE 7

Comparison of Large Scale rAAV Virion Production Obtained Using Adenoviral-Based or Plasmid-Based Accessory Functions In order to compare large scale preparations of rAAV virions produced using either adenovirus type-2 (ad-2) based, or pladeno 1 based accessory functions, the following experiment was carried out.

Approximately $10^9$ 293 cells were transfected with an AAV vector containing the human erythropoietin gene using the transfection method described in Example 1. One preparation was co-transfected with the pladeno 1 construct, the other preparation was infected with adenovirus type-2 as a source of accessory functions.

After a suitable incubation period, cells from each experimental group were then collected, growth media was removed by centrifugation (1000×g for 10 min.), and a lysate was produced using 3 freeze/thaw cycles (alternating between dry ice-ethanol and 37° C. baths). The lysates were made free of debris by centrifugation (10,000×g for 10 min) to obtain a crude lysate. In order to obtain a purified sample, the crude lysates were subjected to density gradient centrifugation.

The amount of rAAV genomes produced by each preparation was quantified by the dot blot assay described in Example 2. The results of the experiment are depicted below in Table 7.

TABLE 7

|  | Ad-2 | | pladeno 1 | |
|---|---|---|---|---|
|  | genomes | % recovery | genomes | % recovery |
| crude lysate | $6.5 \times 10^{13}$ | 100 | $1.6 \times 10^{14}$ | 100 |
| after purification | $5.5 \times 10^{13}$ | 85 | $8 \times 10^{13}$ | 50 |

As can be seen from the results in Table 7, the preparation using the pladeno 1-based accessory functions provided a rAAV virion yield that was 2.4 fold greater than that obtained from the preparation using the adenovirus type-2 based accessory functions.

EXAMPLE 8

Determination of the Relative Contributions of Individual Adenoviral Accessory Functions in rAAV Virion Production In order to determine the relative contributions of the individual adenoviral accessory functions in rAAV virion production, the following experiment was carried out. Individual adenoviral accessory functions, either alone, or in combinations, were used to support rAAV virion production in host cells. In addition, the effect of substituting CMV-driven E2a or E4 ORF6 constructs (the p3.3cE2A and p3.3cE4ORF6 constructs, described below), for constructs containing the entire E2a and E4 ORF6 regions and driven by homologous promoters (the pBSII-E2a and pBSII-E4 constructs) was assessed.

1. Construction of p3.3cE2A and p3.3cE4ORF6:

The structural genes encoding the adenovirus type-5 E2a 72 kD DNA-binding protein, and the adenovirus type-5 E4 open reading frame 6 (ORF6) protein, were each cloned into a CMV driven expression construct, p3.3c, to provide the p3.3cE2A and p3.3E4ORF6 plasmid constructs, respectively.

Plasmid p3.3c was constructed as follows. The 2732 bp NotI fragment from p1.1c, which contains pUC119 vector sequences, was ligated to a synthetic DNA fragment containing the following restriction sites: NotI; MluI; Ecl136II; SacII; BstBI; BssHII; SrfI; BssHII; BglII; SnaBI; BstEII; PmlI; RsrII; and NotI. The sequence of the synthetic DNA fragment is:

5'-GCGGCCGCACGCGTGAGCTCCGCGGTTC-GAAGCGCGCAAAGCCCCGGGCAAAGCG CGCA-GATCTACGTAGGTAACCACGTGCGGAC-CGGCGGCCGC-3' (SEQ ID NO:11). A 653 bp SpeI-SacII fragment including the cytomegalovirus immediate early (CMV IE) promoter; a 269 bp PCR-produced BstBI-BstBI fragment encoding the hGH 1st intron that was obtained using the following primers 5'-AAAATTCGAACAGGTAAGCGCCCCTTTG-3' (SEQ ID NO:12) and 3'-AAAATTCGAATCCTGGG-GAGAAACCAGAG-5' (SEQ ID NO:13); and a 213 bp BamHI-BamHI (blunted) fragment containing the SV40 late polyadenylation site from pCMV-β (obtained from Clonetech), were cloned into the Ecl136II, BstBI and SnaBI sites of the synthetic linker, respectively, to result in the p3.3c expression construct.

Plasmid p3.3cE4ORF6 (ATCC Accession Number 98234) was prepared as follows. The 1024 bp BglII-SmaI fragment from pBSII-E4, containing sequences encoding the adenovirus type-5 E4 ORF6, was obtained and blunt end-modified.

This fragment corresponds to position 33,309 (SmaI site) through position 34,115 (BglII site) of the adenovirus type-2 genome. The modified fragment was then cloned into the SrfI site of p3.3c to provide the p3.3cE4ORF6 plasmid.

Plasmid p3.3cE2A (ATCC Accession Number 98235) was prepared as follows. The 2467 bp MscI(partial)-BamHI fragment from pBSII-E2a was obtained. This fragment contains adenovirus type-5 E2a coding sequences and corresponds to positions 24,073 (MscI site) through 21,606 (BamHI site) of the adenovirus type-2 genome. The 2467 bp fragment was subcloned between the MscI and BamHI sites of pCITE2A (obtained from Novagene) to provide the pCITE2AE2A construct. The 1636 bp NcoI(partial)-BsrGI fragment was then excised from pCITE2AE2A. This fragment contains sequences encoding the E2a 72 kD protein, and corresponds to positions 24,076 (MscI/NcoI site) through 22,440 (BsrGI site) of the adenovirus type-2 genome. The 1636 bp fragment was blunt end-modified, and cloned into p3.3c to provide the p3.3cE2A plasmid.

2. rAAV Virion Production Assay:

293 cells were plated in 10-cm tissue culture dishes at $2 \times 10^6$ cells/dish, and were cultured at 37° C. to reach approximately 90% confluency over a period of about 48 hours prior to co-transfections. All transfections were carried out using the $CaPO_4$ method with the following combinations of DNAs. All of the 293 cell cultures were transfected with 5 μg of the plasmid pW620adhlacZ. 5 μg of various accessory function constructs (as shown in Table 8 below) were used to provide a total of 20 μg DNA per dish. For samples receiving less than 4 constructs, pBSII DNA was used to bring the total amount of transfected DNA to 20 μg. After the transfections, the media was replaced, and cultures using adenovirus for accessory functions received adenovirus type-2 at a MOI of 5. All cultures were then incubated at 37° C. for approximately 72 hours prior to harvest.

Cells from each dish were then collected, media was removed by centrifugation (1000×g for 10 min.), and a 1 mL lysate was produced using 3 freeze/thaw cycles (alternating between dry ice-ethanol and 37° C. baths). The lysates were made free of debris by centrifugation (10,000×g for 10 min). rAAV lacZ virion production was then assessed using the techniques described in Example 1. The lacZ titering was done in the presence of adenovirus. All samples were assayed in duplicate. The results from the experiment are depicted below in Table 8.

TABLE 8

| Adenoviral Accessory Functions | AAV Titer† |
|---|---|
| ad-2 (moi = 5) | $4 \times 10^8$ |
| pBSII-E2a, pBSII-E4, pBSII-VA RNAs | $6 \times 10^8$ |
| pladeno 1 | $8 \times 10^8$ |
| pBSII-E2a | $8 \times 10^6$ |
| PBSII-E4 | $<10^4$ |
| pBSII-VA RNAs | $5 \times 10^4$ |
| pBSII-E4, pBSII-VA RNAs | $1 \times 10^5$ |
| pBSII-E2a, pBSII-VA RNAs | $6 \times 10^7$ |
| pBSII-E2a, pBSII-E4 | $1 \times 10^8$ |
| p3.3cE2A, pBSII-E4, pBSII-VA RNAs | $4 \times 10^8$ |
| pBSII-E2a, p3.3cE4ORF6, pBSII-VA RNAs | $3 \times 10^8$ |
| p3.3cE2A, p3.3cE4ORF6, pBSII-VA RNAs | $4 \times 10^8$ |

†As determined by the lacZ assay.

As can be seen by the results depicted in Table 8, the adenoviral E2a, E4 and VA RNA regions are all necessary to provide efficient rAAV virion production (at levels substantially equivalent to those obtained using adenovirus infection to provide the accessory functions). However, no single one of those regions is absolutely required for rAAV virion production.

The E2a and E4 regions that are subcloned into the pBSII-E2a and pBSII-E4 constructs contain several open reading frames (ORFs) in addition to the ORFs for the 72 kD E2a DNA binding protein and the E4 ORF6-protein. By substituting the CMV-driven p3.3cE2A and p3.3cE4ORF6 constructs for the pBSII-E2a and pBSII-E4 constructs in the above-described study, it has now been established that the E2a 72 kD DNA-binding protein and the E4 ORF6 protein are capable of providing full E2a or E4 accessory function in the absence of all other open reading frames from their respective coding regions.

EXAMPLE 9

Reconstruction of the Pladeno 1 Plasmid and Comparison of rAAV Virion Production Efficiency The pladeno 1 plasmid was reconstructed using purified adenovirus type-2 DNA as a source of the adenoviral genes in place of the pJM17-derived adenovirus genes that were used in the construction of pladeno 1. The reconstructed plasmid, termed pladeno 5, is described in detail below. This reconstruction was carried out to reduce the overall size of the plasmid. Furthermore, the reconstructed plasmid (pladeno 5) does not encode the adenovirus protease, whereas pladeno 1 does.

1. Construction of Pladeno 5:

The pladeno 5 plasmid was constructed as follows. DNA fragments encoding the E2a, E4 and VA RNA regions isolated from purified adenovirus type-2 DNA (obtained from Gibco/BRL) were ligated into a plasmid called pAmpscript. The pAmpscript plasmid was assembled as follows: oligonucleotide-directed mutagenesis was used to eliminate a 623 bp region including the polylinker and alpha complementation expression cassette from pBSII s/k+ (obtained from Stratagene), and to replace it with an EcoRV site. The sequence of the mutagenic oligo used on the oligonucleotide-directed mutagenesis was
5'-CCGCTACAGGGCGCGATATCAGCTCACTCAA-3' (SEQ ID NO:14). A polylinker (containing the following restriction sites: BamHI; KpnI; SrfI; XbaI; ClaI; Bst1107I; SalI; PmeI; and NdeI) was synthesized and inserted into the EcoRV site created above such that the BamHI side of the linker was proximal to the f1 origin in the modified plasmid to provide the pAmpscript plasmid. The sequence of the polylinker was
5'-GGATCCGGTACCGCCCGGGCTCTA-GAATCGATGTATACGTCGACGTTTAAACCAT ATG-3' (SEQ ID NO:15).

DNA fragments comprising the adenovirus type-2 E2a and VA RNA sequences were cloned directly into pAmpscript. In particular, a 5962 bp SrfI-KpnI(partial) fragment containing the E2a region was cloned between the SrfI and KpnI sites of pAmpscript. The 5962 bp fragment comprises base pairs 21,606-27,568 of the adenovirus type-2 genome. A 732 bp EcoRV-SacII(blunted) fragment containing the VA RNAs was cloned into the Bst1107I site of pAmpscript. The 732 bp fragment is equivalent to base pairs 10,423-11,155 of the adenovirus type-2 genome.

The DNA comprising the adenovirus type-2 E4 sequences had to be modified before it could be inserted into the pAmpscript polylinker. Specifically, PCR mutagenesis was used to replace the E4 proximal, adenoviral terminal repeat with a SrfI site. The location of this SrfI site is equivalent to base pairs 35,836-35,844 of the adenovirus type-2 genome. The sequences of the oligonucleotides used in the mutagenesis were:

5'-AGAGGCCCGGGCGTTTTAGGGCGGAG-TAACTTGC-3' (SEQ ID NO:16); and 5'-ACATACCCG-CAGGCGTAGAGAC-3' (SEQ ID NO:17). A 3,192 bp E4 fragment, produced by cleaving the above-described modified E4 gene with SrfI and SpeI, was ligated between the SrfI and XbaI sites of pAmpscript which already contained the E2a and VA RNA sequences to result in the pladeno 5 plasmid. The 3,192 bp fragment is equivalent to base pairs 32,644-35,836 of the adenovirus type-2 genome.

2. rAAV Virion Production Assay:

293 cells were plated in 10-cm tissue culture dishes at $1 \times 10^6$ cells/dish, and were cultured at 37° C. to reach approximately 90% confluency over a period of from about 24 to 48 hours prior to co-transfections. All transfections were carried out as described above in Example 1.

The 293 cell cultures were transfected with 5 μg of the pVlacZ vector plasmid, 5 μg of plasmid pW1909, and 5 μg of either pladeno 1 or pladeno 5. After the transfections, the media was replaced, and the cultures were incubated at 37° C. for approximately 72 hours before harvest.

Cells from each experimental group were then collected, media was removed by centrifugation (1000×g for 10 min.), and a 1 mL lysate was produced using 3 freeze/thaw cycles (alternating between dry ice-ethanol and 37° C. baths). The lysates were made free of debris by centrifugation (10,000×g for 10 min). rAAV lacZ virion production was then assessed using the techniques described in Example 1. The results from the experiment are depicted below in Table 9

TABLE 9

| Accessory Function Vector | rAAV Titer† |
|---|---|
| pladeno 1 | $2.2 \times 10^9$ |
| pladeno 5 | $5.5 \times 10^9$ |

†As determined by the lacZ assay.

As can be seen by the results reported in Table 9, greater rAAV virion production efficiency was seen when using pladeno 5 (pladeno 5 production yielded 2.5 fold more rAAV virions than pladeno 1 production).

Accordingly, novel accessory functions capable of supporting efficient recombinant AAV virion production have been described. Although preferred embodiments of the subject invention have been described in some detail, it is understood that obvious variations can be made without departing from the spirit and the scope of the invention as defined by the appended claims.

Deposits of Strains Useful in Practicing the Invention

A deposit of biologically pure cultures of the following strains was made with the American Type Culture Collection, 12301 Parklawn Drive, Rockville, Md., under the provisions of the Budapest Treaty. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. Upon the granting of a patent-in this application, all restrictions imposed by the depositor on the availability to the public of the deposited biological material will be irrevocably removed with the following one exception, as specified in 37 C.F.R. §1.808(b), said exception being that depositor reserves the right to contract with the depository to require that samples of the deposited material be furnished only if a request for a sample, during the term of the issued patent, meets any one, or all, of the following three conditions: (1) the request is in writing or other tangible form and dated; and/or (2) the request contains the name and address of the requesting party and the accession number of the deposit; and/or (3) the request is communicated in writing by the depository to the depositor along with the date on which the sample was furnished and the name and address of the party to whom the sample was furnished. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, lose its plasmid, it will be replaced with a viable culture(s) of the same-taxonomic description.

These deposits are provided merely as a convenience to those of skill in the art, and are not an admission that a deposit is required. The nucleic acid sequences of these plasmids, as well as the amino sequences of the polypeptides encoded thereby, are controlling in the event of any conflict with the description herein. A license may be required to make, use, or sell the deposited materials, and no such license is hereby granted.

| Strain | Deposit Date | ATCC No. |
|---|---|---|
| pBSII-VA RNAs | Oct. 30, 1996 | 98233 |
| p3.3cE4ORF6 | Oct. 30, 1996 | 98234 |
| p3.3cE2A | Oct. 30, 1996 | 98235 |
| pGN1909 | Jul. 20, 1995 | 69871 |

The invention claimed is:

1. A nucleic acid molecule which provides one or more accessory functions for supporting recombinant AAV (rAAV) virion production in a suitable host cell and that lacks at least one adenoviral late gene region, said molecule comprising a nucleotide sequence selected from the group consisting of (i) a sequence that provides adenovirus VA RNAs, (ii) an adenovirus E4 ORF6 coding region, (iii) an adenovirus E2a 72 kD coding region, and any combination of nucleotide sequences (i), (ii) and (iii).

2. An accessory function vector comprising the nucleic acid molecule of claim 1.

3. The accessory function vector of claim 2, wherein said vector is a plasmid.

4. The accessory function vector of claim 3 further comprising at least one heterologous promoter region operably linked to said nucleotide sequence.

5. The accessory function vector of claim 4 wherein the at least one heterologous promoter region comprises a nucleotide sequence substantially homologous to the cytomegalovirus (CMV) immediate early promoter region.

6. A nucleic acid molecule which provides accessory functions for supporting efficient recombinant AAV (rAAV) virion production in a suitable host cell and that lacks at least one adenoviral late gene region.

7. The nucleic acid molecule of claim 6, wherein said nucleic acid molecule lacks adenoviral early gene regions 2b and 3.

8. The nucleic acid molecule of claim 6, which provides accessory functions capable of supporting efficient rAAV virion production in a human 293 host cell.

9. The nucleic acid molecule of claim 8, comprising one or more nucleotide sequences derived from an adenovirus type-2 or type-5 genome.

10. The nucleic acid molecule of claim 9, comprising:
a first nucleotide sequence that provides an adenovirus VA RNA;
a second nucleotide sequence comprising an adenovirus E4 coding region containing the ORF 6; and
a third nucleotide sequence comprising an adenovirus E2a coding region.

11. The nucleic acid molecule of claim 6, wherein the nucleic acid molecule provides accessory functions capable of supporting efficient recombinant AAV (rAAV) virion production in a suitable host cell that is not infectable by adenovirus or is not capable of supporting adenovirus replication.

12. The nucleic acid molecule of claim 11, comprising one or more nucleotide sequences derived from an adenovirus type-2 or type-5 genome.

13. The nucleic acid molecule of claim 12, comprising:
a first nucleotide sequence that provides an adenovirus VA RNA;
a second nucleotide sequence comprising an adenovirus E4 coding region containing the ORF 6;
a third nucleotide sequence comprising an adenovirus E2a coding region; and
a fourth nucleotide sequence comprising the adenovirus E1a and E1b coding regions.

14. An accessory function vector comprising the nucleic acid molecule of claim 6.

15. The accessory function vector of claim 14, wherein said vector is a plasmid.

16. An accessory function vector comprising the nucleic acid molecule of claim 11.

17. The accessory function vector of claim 16, wherein said vector is a plasmid.

18. The accessory function vector of claim 15 further comprising a selectable genetic marker.

19. The accessory function vector of claim 18, wherein the selectable genetic marker comprises an antibiotic resistance gene.

20. The accessory function vector of claim 15 further comprising at least one heterologous promoter region.

21. The accessory function vector of claim 20, wherein the at least one heterologous promoter region comprises a nucleotide sequence substantially homologous to the cytomegalovirus (CMV) immediate early promoter region.

22. A host cell that has been transfected with the accessory function vector of claim 2.

23. A host cell that has been transfected with the accessory function vector of claim 14.

24. A host cell that has been transfected with the accessory function vector of claim 16.

25. A cell capable of producing recombinant AAV (rAAV) virions when transfected with an AAV vector, said cell comprising the host cell of claim 23 co-transfected with an AAV helper construct that is capable of being expressed in said cell to provide AAV helper functions.

26. A method of producing recombinant AAV (rAAV) virions, comprising:
(a) introducing an AAV vector into a suitable host cell;
(b) introducing an AAV helper construct into the host cell, said helper construct comprising AAV coding regions that are expressed in the host cell to complement AAV helper functions missing from said AAV vector;
(c) introducing the accessory function vector of claim 14 into the host cell, said accessory function vector providing accessory functions for supporting efficient rAAV virion production in the host cell; and (d) culturing the host cell to produce rAAV virions.

27. A method of producing recombinant AAV (rAAV) virions in a host cell that is not infectable by adenovirus or is not capable of supporting adenovirus replication, comprising:

(a) introducing an AAV vector into the host cell;

(b) introducing an AAV helper construct into the host cell, said helper construct comprising AAV coding regions that are expressed in the host cell to complement AAV helper functions missing from said AAV vector;

(c) introducing the accessory function vector of claim 16 into the host cell, said accessory function vector providing accessory functions for supporting efficient rAAV virion production in the host cell; and (d) culturing the host cell to produce rAAV virions.

* * * * *